United States Patent [19]

Holmes

[11] Patent Number: 5,550,215

[45] Date of Patent: Aug. 27, 1996

[54] POLYMER REVERSAL ON SOLID SURFACES

[76] Inventor: Christopher P. Holmes, 521 Pine Ave., Sunnyvale, Calif. 94086

[21] Appl. No.: 351,058

[22] Filed: Nov. 28, 1994

Related U.S. Application Data

[63] Continuation of Ser. No. 978,940, Nov. 19, 1992, abandoned, which is a continuation-in-part of Ser. No. 796,727, Nov. 22, 1991, Pat. No. 5,242,974.

[51] Int. Cl.$^6$ .............................. C07H 1/00; C07K 1/04; C08B 37/00; C08F 283/00
[52] U.S. Cl. ...................... 530/334; 525/54.11; 536/25.3; 536/126
[58] Field of Search ........................... 536/25.3, 25.31, 536/124, 126; 530/317, 318, 319, 320, 321, 332, 334, 345, 335, 336, 337; 525/54.11, 54.2

[56] References Cited

U.S. PATENT DOCUMENTS

| | | | |
|---|---|---|---|
| 4,772,906 | 2/1988 | Guire | 436/501 |
| 5,004,781 | 4/1991 | Rink | 525/54.11 |
| 5,064,907 | 11/1991 | Bronstert et al. | 525/54.11 |
| 5,066,716 | 11/1991 | Robey et al. | 525/54.11 |
| 5,143,854 | 9/1992 | Pirrung et al. | 436/518 |
| 5,242,974 | 9/1993 | Holmes | 530/334 |

FOREIGN PATENT DOCUMENTS

| | | | |
|---|---|---|---|
| 9015070 | 12/1990 | WIPO | C07K 1/04 |
| 9210092 | 6/1992 | WIPO | A01N 1/02 |

OTHER PUBLICATIONS

Bodanszky, Principles of Peptide Synthesis, published 1984 by Springer–Verlag (NY), pp. 67–68.
Lin, et al., *Distinct Requirements for Activation at CCK–A and CCK–B/Gastrin Receptors: Studies with a C–Terminal Hydrazide Analogue of Cholecystokinin Tetrapeptide (30–33)*, Molecular Pharmacology, 36:881–886 (1989).
J. Am. Chem. Soc., vol. 116, issued 1994, Kanla et al, "Free C–Terminal Resin–Bound Peptides . . . ", pp. 8835–8836.
Epton, "Innovation and Perspectives in Solid Phase Synthesis", published 1994 by Mayflower Worldwide Ltd. (Birmingham), pp. 233–238.
Peptide Science, issued Feb. 1995, Lebl et al, "One–Bead–One–Structure Combinatorial Libraries".
USSN 07/624,120 entitled "Very Large Scale Immobilized Polymer Synthesis" (Fodor et al.).
Bodanszky, *Priciples of Peptide Synthesis*, Springer–Verlag, 1984, pp. 208–229.
Rovero et al., Tetrahedron Letters, (1991) 32:2639–2642.
McMurray, *Tetrahedron Letters*, (1991) 32:7679–7682.
Fodor et al., Science, 1991 251:767–773 Light–directed, spatially addressable parallel chemical synthesis.
Geysen et al., J. Imm. Meth., 1987 102:259–274 Strategies for epitope analysis using peptide synthesis.
Albericio, F. "Allyl–based orthogonal solid phase peptide synthesis" *Peptides* Sep. 1992, pp. 191–193.
Almquist et al. (1989) Int. J. Peptide Protein Res. 34:455–462.
Plaue (1990) Int. J. Peptide Protein Res. 35:510–517.
Isied et al. (1982) J. Am. Chem. Soc. 104:2632–2634.
Al–Obeidi et al. (1989) J. Med. Chem. 32:2555–2561.
Lebl et al. (1984) Tett. Lett. 25(20):2067–2068.
Felix et al. (1988) Int. J. Peptide Res. 31:231–238.
Ploux et al. (1987) Int. J. Peptide Res. 29:162–169.
McMurray (1991) Tett. Lett. 32(52):7679–7682.
Trzeciak et al. (1992) Tett. Lett. 33(32):4557–4560.

Primary Examiner—Jeffrey E. Russel

[57] ABSTRACT

A method for cyclization and reversal of the polarity of polymers on a substrate. The method provides for the formation of a polymer on a substrate (2) with a tether molecule (4). Through unmasking of a protective group (PG$_2$) a cyclic polymer (6) is formed. Through cleavage of an appropriate bond, a polarity reversed polymer (8) is formed. The method finds particular application in the formation of, for example, peptides and oligonucleotides.

16 Claims, 16 Drawing Sheets

GENERAL             PREFERRED
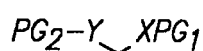
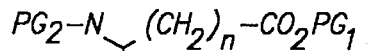
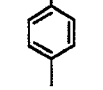
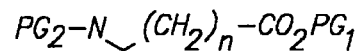
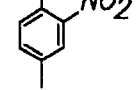
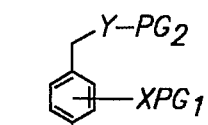
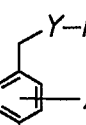
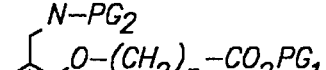
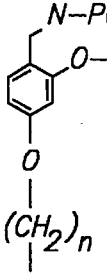
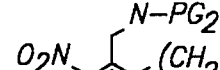
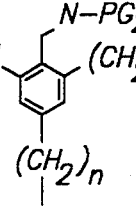
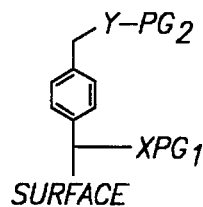
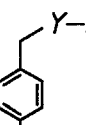
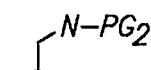
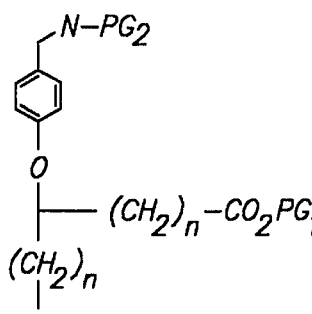
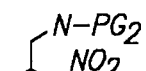
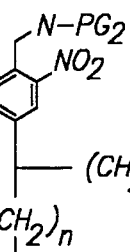
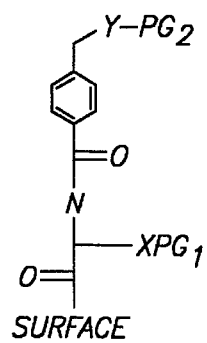
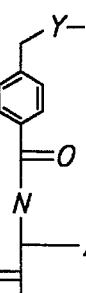
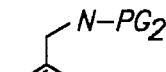
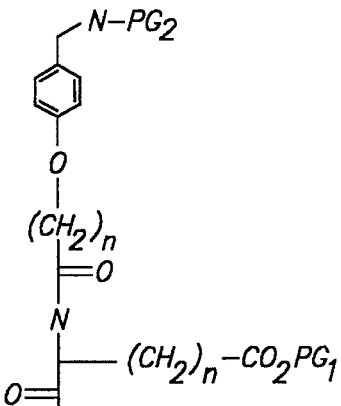
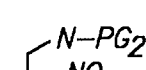
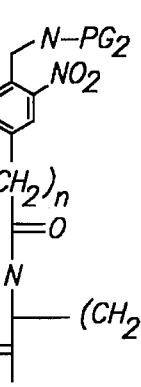
FIG. 3       ACID CLEAVAGE       PHOTOLYTIC CLEAVAGE

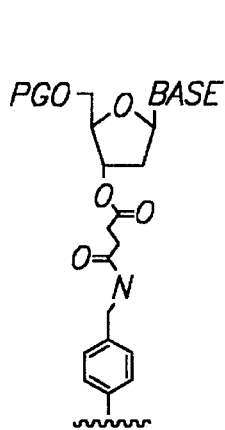 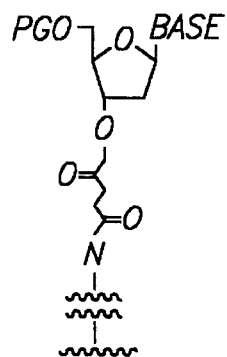 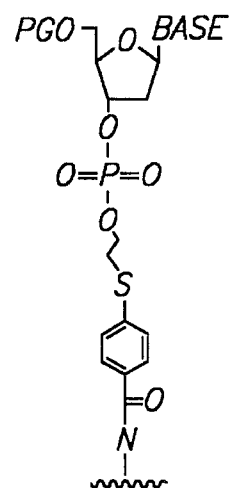
FIG. 4a        FIG. 4b        FIG. 4c
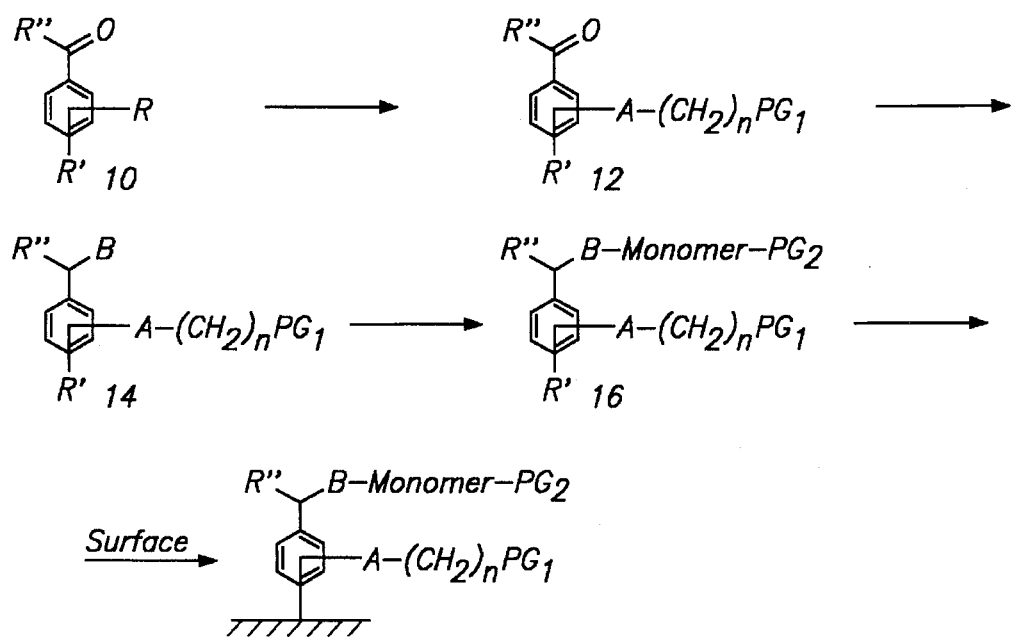
FIG. 6

| STEP | MASK | BUILDING BLOCK |
|---|---|---|
| 1 | | NVOC-GLU-OFM  (Cycle) |
| 2 | | |
| 3-8 | | NVOC-Phe,Asp,Met,Trp,Gly,Met-OH |
| 9 | | NVOC-N-CAPROIC-OH (CAP) |

| 1 | 3 | 5 | 7 |
|---|---|---|---|
| 2 | 4 | 6 | 8 |

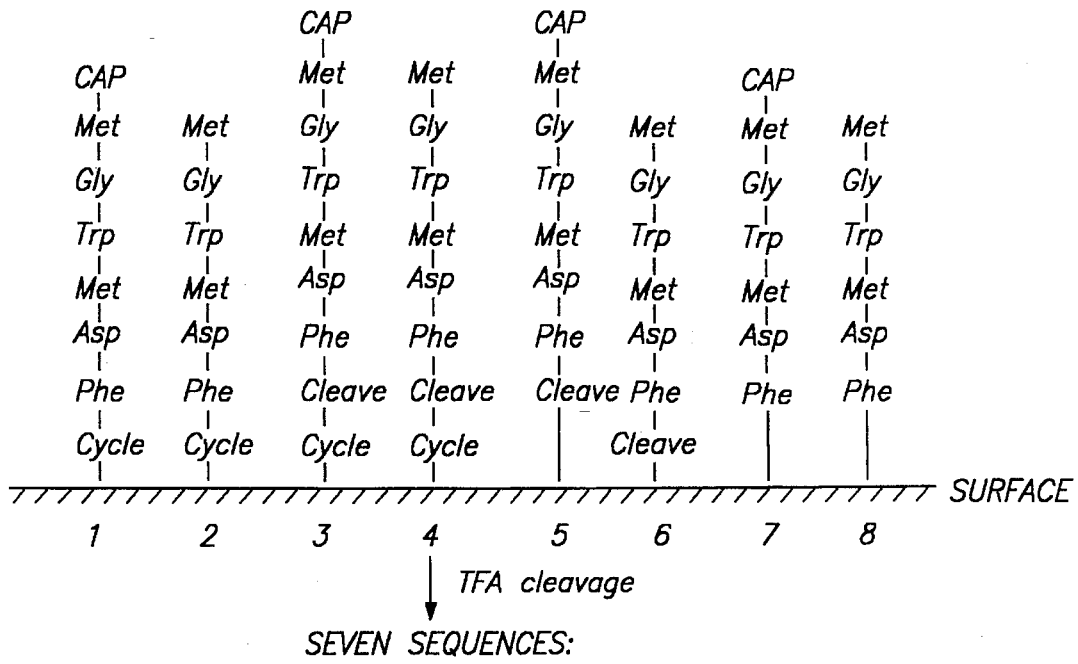
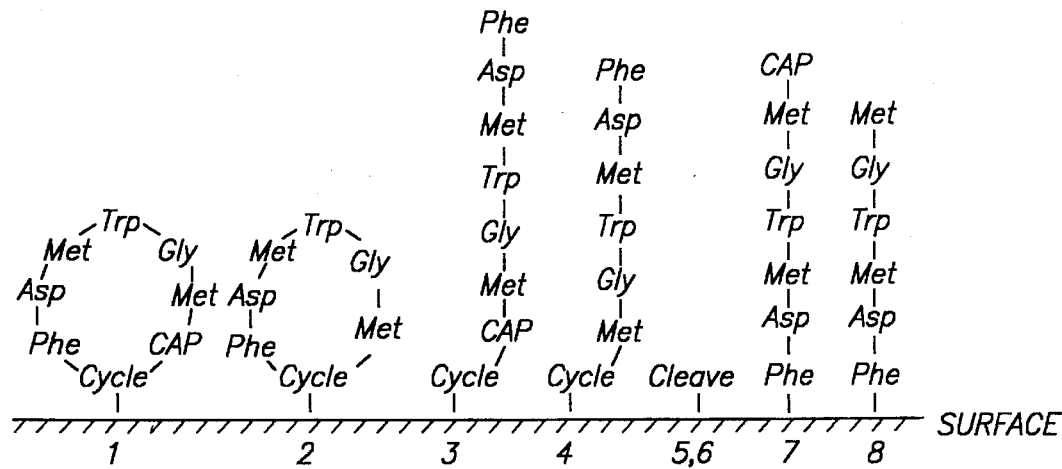
FIG. 14b

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Pro  Pro  Pro  Pro
1

( 2 ) INFORMATION FOR SEQ ID NO:2:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Ala  Ala  Ala  Ala
1

( 2 ) INFORMATION FOR SEQ ID NO:3:

( i ) SEQUENCE CHARACTERISTICS:
( A ) LENGTH: 4 amino acids
( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:3:

Ala Gly Gly Gly
1

( 2 ) INFORMATION FOR SEQ ID NO:4:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

Val Val Val Val
1

( 2 ) INFORMATION FOR SEQ ID NO:5:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

Pro Pro Pro Pro Glu
1               5

( 2 ) INFORMATION FOR SEQ ID NO:6:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:6:

Ala Ala Ala Ala Glu
1               5

( 2 ) INFORMATION FOR SEQ ID NO:7:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:7:

Ala Gly Gly Gly Glu
1               5

( 2 ) INFORMATION FOR SEQ ID NO:8:

( i ) SEQUENCE CHARACTERISTICS:
( A ) LENGTH: 5 amino acids
( B ) TYPE: amino acid

```
          ( C ) STRANDEDNESS: single
          ( D ) TOPOLOGY: linear ( i i ) MOLECULE TYPE: peptide ( x i ) SEQUENCE DESCRIPTION: SEQ ID NO:8:

Val  Val  Val  Val  Glu
      1                   5

( 2 ) INFORMATION FOR SEQ ID NO:9:

( i ) SEQUENCE CHARACTERISTICS:
          ( A ) LENGTH: 6 amino acids
          ( B ) TYPE: amino acid
          ( C ) STRANDEDNESS: single
          ( D ) TOPOLOGY: linear ( i i ) MOLECULE TYPE: peptide ( x i ) SEQUENCE DESCRIPTION: SEQ ID NO:9:

Tyr  Gly  Gly  Phe  Leu  Glu
      1                   5

( 2 ) INFORMATION FOR SEQ ID NO:10:

( i ) SEQUENCE CHARACTERISTICS:
          ( A ) LENGTH: 7 amino acids
          ( B ) TYPE: amino acid
          ( C ) STRANDEDNESS: single
          ( D ) TOPOLOGY: linear ( i i ) MOLECULE TYPE: peptide ( x i ) SEQUENCE DESCRIPTION: SEQ ID NO:10:

Met  Gly  Trp  Met  Asp  Phe  Glu
      1                   5

( 2 ) INFORMATION FOR SEQ ID NO:11:

( i ) SEQUENCE CHARACTERISTICS:
          ( A ) LENGTH: 6 amino acids
          ( B ) TYPE: amino acid
          ( C ) STRANDEDNESS: single
          ( D ) TOPOLOGY: linear ( i i ) MOLECULE TYPE: peptide ( x i ) SEQUENCE DESCRIPTION: SEQ ID NO:11:

Met  Gly  Trp  Met  Asp  Phe
      1                   5
```

POLYMER REVERSAL ON SOLID SURFACES

CROSS-REFERENCE TO RELATED APPLICATIONS

This application is a continuation of U.S. patent application Ser. No. 07/978,940, filed Nov. 19, 1992, now abandoned, which, in turn, is a continuation-in-part of U.S. patent application Ser. No. 07/796,727, filed Nov. 22, 1991, now U.S. Pat. No. 5,242,974.

BACKGROUND OF THE INVENTION

The interaction of a molecular recognition element (MRE) or receptor with a surface-bound ligand varies substantially depending on how the ligand is presented. One important consideration in the presentation of a ligand to a receptor is the polarity of the ligand. In other words, a polymer/ligand will interact with a receptor differently in many instances when one "end" of the polymer is presented than when the opposite end is presented by the substrate. Such differential interaction is well known in the art for antibodies and corresponding antigens as well as enzymes and corresponding enzyme substrates (see Walsh, *Enzymatic Reaction Mechanisms,* W. H. Freeman and Co., New York, 1979, incorporated herein by reference for all purposes, for various examples of this differential interaction for enzymes and enzyme substrates).

Many molecules of biological interest, such as peptides, oligonucleotides, and carbohydrates, have an inherent polarity. For example peptides have an inherent polarity at their N and C termini, while oligonuleotides have inherent polarity in their 3' and 5' termini. Oligosaccharides also have an inherent polarity, having at least one hydroxyl group at one "end" and an anomeric center, with substantially different chemical reactivity at the other. The choice of which "end" of the polymer is to be tethered to a substrate during synthesis is generally governed by the chemistry required to build the polymer using solid-phase synthesis techniques. Peptides, for example, are frequently anchored to a substrate via their carboxyl terminus and the chemical synthesis proceeds on the terminal amino group (termed C to N or "Merrifield" synthesis) whereas nucleotides frequently have their 3' end anchored and the synthesis proceeds on the 5' end. Oligosaccharide solid-phase synthesis likewise proceeds with one end anchored and the other end available for reaction during synthesis.

Use of surface-bound ligands as a screening tool has necessitated the development of novel chemistries to provide for the presentation of polymers with both complementary polarities. For instance, proteins are typically sequenced from the amino terminus, but newer methods, see U.S. Pat. No. 5,064,767, incorporated herein by reference, provide for sequencing from the carboxyl terminus. Some have proposed that the polymers be fully synthesized and then attached to a solid support with reversed polarity. This is often a labor-intensive and inefficient process. In the case of peptides, one may alternatively simply reverse the direction of synthesis of the polymer so as to anchor the molecule via the terminal amino group and proceed with the synthesis on the carboxyl terminus (termed "N to C synthesis").

There are several reasons why conventional polymer synthesis techniques cannot be easily adapted to the synthesis of polymers having their "opposite" terminus exposed, where exposed refers to the end of the polymer not attached to the solid support. In the case of peptides, for example, one problem, although not fully understood, is believed to be racemization of the growing peptide chain in a reversed polymer synthesis scheme. Racemization has been proposed to occur via intramolecular attack of the amide oxygen of the adjacent residue on the activated ester of the terminal residue, leading to an intermediate oxazolinone prone to racemization. While prevention of racemization may be possible, it may be a difficult, costly, or complex problem to solve. This problem may be particularly difficult to solve in the case of synthesis of polymers of substantial length. For example, in a 10-step synthesis there will often be 9 possible racemization events producing up to $2^9=512$ diastereomers.

In the case of nucleotide synthesis other problems are also not fully understood, but are believed to present difficulties. For example, there may be difficulty in selectively protecting the two types of hydroxyl groups (secondary versus primary) and the relative stabilities of the resultant compounds.

From the above it is seen that improved means and methods of synthesizing and presenting polymers on surfaces are desired.

SUMMARY OF THE INVENTION

Improved means and methods for synthesizing and presenting polymers on solid surfaces are disclosed. The methods are particularly useful in synthesizing polymers in reverse from a direction of normal synthesis, and for forming cyclic polymers. The invention also provides for a novel class of linkers (i.e., tether molecules) having three sites of reactivity and orthogonal cleavage protocols.

According to one specific embodiment, the invention provides a method having a first step in which polymers are formed using standard polymer synthesis (Merrifield peptide synthesis or conventional nucleotide synthesis for example), or more advanced techniques, such as light-directed, spatially-addressable techniques. The polymers thus formed have a first polarity. Thereafter, the method provides for the unmasking of a reactive moiety on a tether molecule linking the polymer(s) to the surface. This activation allows for subsequent cyclization of an exposed end or region of the polymer to the reactive moiety on the linker. The method may optionally involve cleavage of the bond anchoring the polymer to the tether (the "Y—A" bond shown below), whereby a reversed sequence is formed, i.e., whereby the polarity of the molecule is reversed from the first polarity.

Accordingly, one embodiment of the invention provides for a method of synthesizing a polymer on a substrate comprising the steps of, on a surface of the substrate, providing a molecule having the general formula:

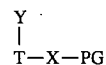

where X and Y are first and second reactive sites, respectively, T is a tether molecule, and PG is a first protective group; coupling a polymer to the reactive site Y; removing the protective group PG; and coupling a portion of the polymer to the tether at the first reactive site. The method may further provide for the step of reversing the polarity of the polymer by separating the polymer from the reactive site Y. In some embodiments of the invention, a protecting group on X is unnecessary because X is unreactive under the conditions used for coupling of monomers to Y.

A further understanding of the nature and advantages of the inventions herein may be realized by reference to the remaining portions of the specification and the attached drawings.

BRIEF DESCRIPTION OF THE DRAWINGS

FIG. 3 shows preferred examples of four types of benzylic tether molecules and their modes of cleavage;

FIGS. 4a to 4c illustrate existing nucleotide tethers;

FIG. 6 provides an exemplary process for the synthesis of type II benzylic tethers and their attachment and use;

FIG. 14a and 14b (SEQ ID NOS: 10, 11) shows the masking protocol for the synthesis of an array of peptides;

DETAILED DESCRIPTION OF THE INVENTION

TABLE OF CONTENTS

Figure 1A:
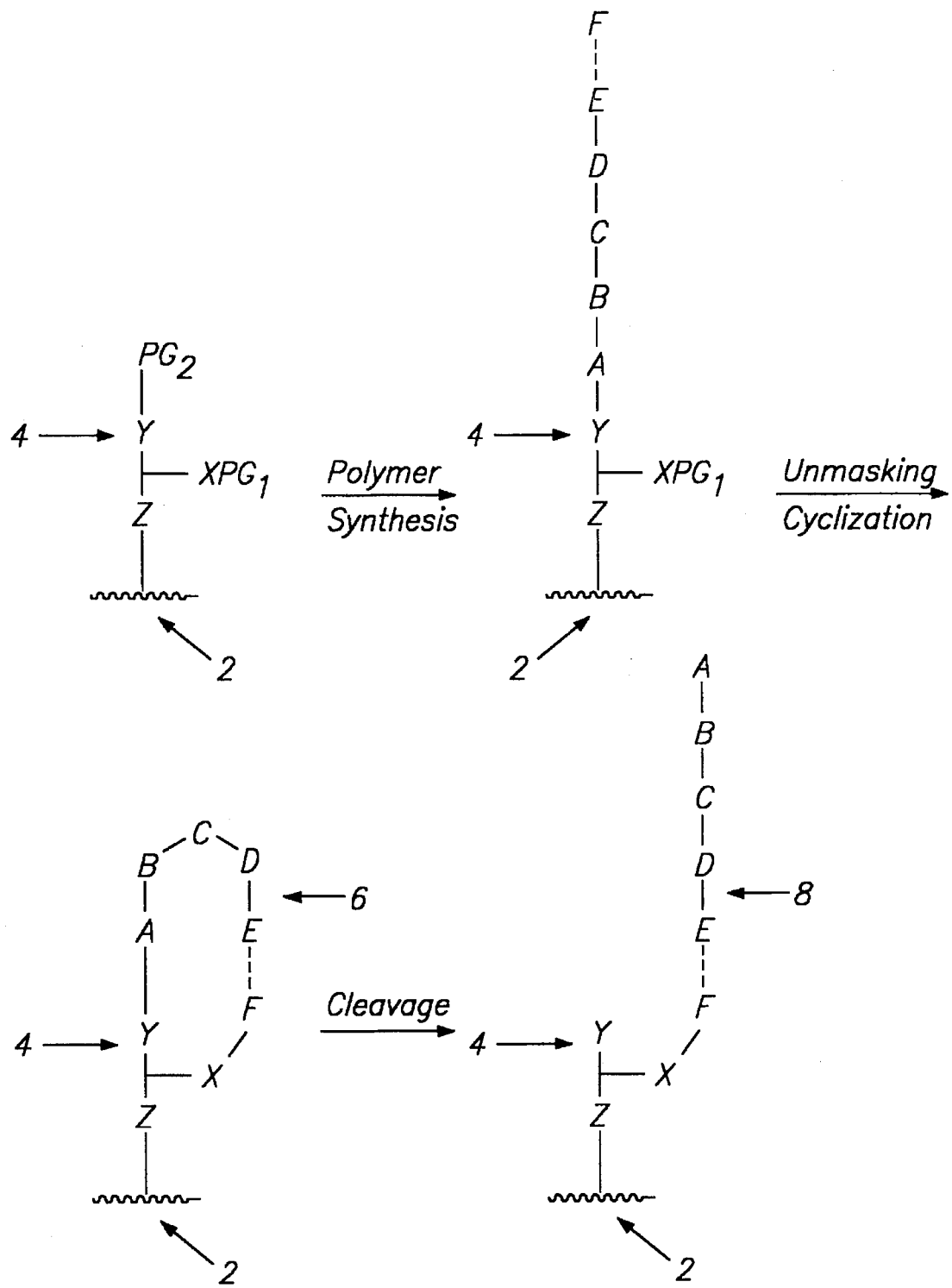
FIG. 1a and 1b are overall flow diagrams illustrating one aspect of the invention.

I. Definitions and Terminology
II. Overall Description of the Invention
III. Detailed Description Protective of Preferred Embodiments
  A. Protective groups
    1. Conventional Peptide Synthesis
    2. VLSIPS™ Peptide Synthesis
    3. Conventional Oligonucleotide Synthesis
    4. VLSIPS™ Oligonucleotide Synthesis
    5. Other Polymers
  B. Cyclization
  C. Tether Molecules
    1. Peptides
      a) Amino acid tethers
      b) Benzylic tethers
      c) Miscellaneous tethers
    2. Oligonucleotides
IV. Use of the Synthesized Polymers
V. Examples
  A. Tether Attachment - Overall Description
  B. Examples
    1. Type I Benzylic Tethers
    2. Type II Benzylic Tethers
    3. Specific Embodiment
      a) First Specific Embodiment
      b) Second Specific Embodiment
      c) Third Specific Embodiment
      d) Fourth Specific Embodiment
  C. Cyclization
    1. First Specific Embodiment
    2. Second Specific Embodiment
  D. Polymer Reversal
    1. First Specific Embodiment
VI. Conclusion I. Definitions and Terminology The following terms are intended to have the following general meanings as they are used herein:

1. Ligand: A ligand is a molecule that is recognized by a particular receptor. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, cofactors, drugs, lectins, sugars, oligonucleotides, nucleic acids, oligosaccharides, proteins, and monoclonal antibodies.

2. Monomer: A member of the set of small molecules which can be joined together to form a larger molecule, especially those having an inherent polarity. The set of monomers includes but is not restricted to, for example, the set of common L-amino acids, the set of D-amino acids, the set of synthetic or natural amino acids, the set of nucleotides and the set of pentoses and hexoses. As used herein, monomers refers to any member of a basis set for synthesis of a polymer. For example, dimers of the 20 naturally occurring L-amino acids form a basis set of 400 monomers for synthesis of polypeptides. Different basis sets of monomers may be used at successive steps in the synthesis of a polymer. The invention is described herein primarily with regard to the preparation of molecules containing sequences of monomers such as amino acids or nucleic acids, but could readily be applied in the preparation of other polymers. Such polymers include, for example, polysaccharides, phospholipids, and peptides having either α-, β-, or ω-amino acids, heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure. Polysaccharides, for example, refer herein to a carbohydrate which can be hydrolyzed into many monosaccharides. Polynucleotides refer to molecules containing a series of nucleotide monomers.

3. Oligomer or Polymer: The oligomer or polymer sequences of the present invention are formed from the chemical or enzymatic addition of monomer subunits. Such oligomers include, for example, both linear, cyclic, and branched polymers of nucleic acids, polysaccharides, phospholipids, and peptides having either α-, β-, or ω-amino acids, heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be readily apparent to one skilled in the art upon review of this disclosure.

4. Peptide: A polymer in which the monomers are alpha amino acids and which are joined together through amide bonds, alternatively referred to as a polypeptide. In the context of this specification it should be appreciated that the amino acids may be, for example, the L-optical isomer or the D-optical isomer. Peptides are often two or more amino acid monomers long, and often 4 or more amino acids long, often 5 or more amino acids long, often 10 or more amino acids long, often 15 or more amino acids long, and often 20 or more amino acid monomers long, for example. Standard abbreviations for amino acids are used (e.g., P for proline). These abbreviations are included in Stryer, *Biochemistry*, Third Ed., 1988, which is incorporated herein by reference for all purposes.

5. Oligonucleotides: An oligonucleotide is a single-stranded DNA or RNA molecule, typically prepared by synthetic means. Those oligonucleotides employed in the present invention will be 50 to 150 nucleotides in length, preferably from 80 to 120 nucleotides, and most preferably about 100 nucleotides, although oligonucleotides of different length may be appropriate. Suitable oligonucleotides may be prepared by the phosphoramidite method described by Beaucage and Carruthers, *Tetra. Letts.* 22:1859–1862 (1981), or by the triester method according to Matteucci, et al., *J. Am. Chem. Soc.,* 103:3185 (1981), both incorporated herein by reference, or by other methods such as commercial automated oligonucleotide synthesizers.

6. Receptor: A molecule that has an affinity for a given ligand. Receptors may be naturally-occurring or man-made molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, enzymes, hormones, opiates, polysaccharides, cells, cellular membranes, and organelles. Receptors are sometimes referred to in the art as anti-ligands. As the term receptors is used herein, no difference in meaning is intended. A "ligand receptor pair" is formed when two macromolecules have combined through molecular recognition to form a complex.

7. Substrate or Support: A material or group of materials having a rigid or semi-rigid surface or surfaces. In many embodiments, at least one surface of the substrate will be substantially flat, although in some embodiments it may be desirable to physically separate synthesis regions for different polymers with, for example, wells, raised regions, pins, etched trenches, or the like. According to other embodiments, the substrate(s) will take the form of beads, resins, gels, microspheres, or other geometric configurations. The substrate is alternatively referred to herein as a support.

8. Protective Group: A material which is bound to a molecule and which may be selectively removed therefrom for exposure of a reactive group. A protective group generally prevents undesired reactions from taking place (such as coupling) until such time as the protective group is removed.

9. Predefined Region: A predefined region is a localized area on a substrate which is, was, or is intended to be used for formation of a selected polymer and is otherwise referred to herein in the alternative as a "selected" region. The predefined region may have any convenient shape, e.g., circular, rectangular, elliptical, wedge-shaped, etc. For the sake of brevity herein, "predefined regions" are sometimes referred to simply as "regions." In some embodiments, a predefined region and, therefore, the area upon which each distinct polymer sequence is synthesized is smaller than about 1 $cm^2$ or less than 1 $mm^2$. In preferred embodiments the regions have an area less than about 10,000 $\mu m^2$ or, more preferably, less than 100 $\mu m^2$. Within these regions, the polymer synthesized therein is preferably synthesized in a substantially pure form. In additional embodiments, a predefined region can be achieved by physically separating the regions (i.e., beads, resins, gels, etc.).

10. Substantially Pure: A polymer is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor. Preferably the region is sufficiently pure such that the predominant species in the predefined region is the desired sequence. According to preferred aspects of the invention, the polymer is 5% pure, more preferably more than 10% pure, preferably more than 20% pure, more preferably more than 80% pure, more preferably more than 90% pure, more preferably more than 95% pure, where purity for this purpose refers to the ratio of the number of ligand molecules formed in a predefined region having a desired sequence to the total number of molecules formed in the predefined region.

11. Polarity: Refers herein to the characteristic of a polymer which has at least a first and a second end, each end having distinctive characteristics. For example, peptides are said to have polarity due to the distinctive characteristics of their N and C termini. Oligonucleotides by way of further example have inherent polarity due to the distinctive characteristics of their 3' and 5' termini. Saccharides have an inherent polarity due to the distinctive chemical reactivity characteristics of the hydroxyl and anomeric termini of saccharides. Most monomers of a polymer show polarity, such as in, e.g., amino acids, nucleotides and saccharides. As used herein, "polarity" and "orientation" are to be considered synonymous.

12. Tether: A molecule which is coupled to a substrate and a polymer, directly or indirectly, and which has at least one reactive site thereon that may be selectively activated for coupling of an exposed portion of the polymer to the reactive site. Such tethers provide additional functionality in preferred embodiments such as for the functionalization of a solid support in order to allow for the polymer synthesis, and for de-coupling of a polymer after cyclization for polarity reversal.

13. Activator: Refers herein to an energy source or reagent which selectively renders one or more reactive sites active, or cleaves a selected bond. One example of an activator is a reagent such as a mild base which removes materials such as fluorenylmethyloxycarbonyl (FMOC) or a strong acid which removes certain protective groups such as BOC derivatives, side chain protective groups, and polymer linkage groups. Another illustration of an activator is light. Other examples of activators include ion beams, electric fields, magnetic fields, electron beams, x-ray, and biological activators such as enzymes, and the like.

14. Linker: Refers to a molecule or group of molecules attached to a substrate and spacing a synthesized tether and/or polymer from the substrate.

15. Reactive Group: Refers to a portion of a molecule which, under selected circumstances performs a desired coupling or cleavage reaction with another moiety. Such coupling may be via covalent, or other types of bonds.

16. Isolation and purification of the compounds and intermediates described herein can be effected, if desired, by any suitable separation or purification procedure such as, for example, filtration, extraction, crystallization, column chromatography, thin-layer chromatography, thick-layer (preparative) chromatography, distillation, or a combination of these procedures. Specific illustrations of suitable separation and isolation procedures can be had by references to the examples hereinbelow. However, other equivalent separation or isolation procedures can, of course, also be used.

17. Abbreviations: The following abbreviations are intended to have the following meanings:

BOC=t-butyloxycarbonyl
BOP=benzotriazol-1-yloxytris(dimethylamino) phosphonium hexafluorophosphate
DBMB=o-(dibromomethyl)benzoyl group
DCC=dicyclohexylcarbodiimide
DMF=N,N-dimethylformamide
DDZ=dimethoxydimethylbenzyloxy
DMT=dimethoxytrityl
DTS=N-α-dithiasuccinoyl
FMOC=fluorenylmethyloxycarbonyl
HBTU=2-(1H-benzotriazol-1-yl)-1,1,3,3-tetramethyluronium hexafluorophosphate
LEV=4-oxopentanoyl
NV=nitroveratryl
NVOC=6-nitroveratryloxycarbonyl and other photoremovable groups
Pac=phenylacyl
PG=protective group
SEM=2-(trimethylsilyl)ethoxymethyloxy
TEOC=2-(trimethylsilyl)ethoxycarbonyl
TFA=trifluoroacetic acid II. Overall Description of the Invention According to the invention herein, reversal of the polarity of a polymer and/or cyclization of the polymer is achieved through the use of appropriate protective group manipulation. According to a specific embodiment, the polarity of a polymer synthesis is reversed, i.e., a previously exposed terminus of the polymer is attached directly or indirectly to the substrate, while a previously directly attached terminus or portion of the polymer is placed in an exposed position.

According to one aspect of the invention the polymer molecules are synthesized with a first polarity on a substrate, and a reactive group on a tether in the polymer molecules is selectively activated. Thereafter, a region, usually a terminal end of the polymer, cyclizes to the tether at the activated site. Optionally, an initial bond joining the polymer to the surface is cleaved, whereby the initially bound group is placed in an exposed position such that the polarity of the polymer is reversed. Specific embodiments of the invention utilize photocleavable or photoactivatable groups as protective groups, while other embodiments use additionally or in combination with the photoactivatable or photocleavable groups a protective or cleavable group that is activated upon exposure to selected reagents such as an acid, base, or biological reagents such as enzymes.

One embodiment of the invention provides for a tether with one, two, three, or more sites of reactivity. A first site (Z) is used to anchor the tether molecule, directly or indirectly via linker molecules to a substrate, preferably via a covalent linkage. A second site (Y) is used to synthesize the polymer with a first polarity, preferably via covalent bonds. A third site (X) is used to cyclize the polymer by bonding a portion of the polymer to the third site, preferably covalently.

According to some embodiments of the invention, the tether has at least one protective group for protection of the third site (X), although a greater number of protective groups will be used according to some embodiments of the invention. For example, one protective group is used in some embodiments for side chain protection on the polymer. Another protective group is used in some embodiments for protection of the end of the polymer on which synthesis is taking place. Still another protective group is used in forming the original linkage between the polymer and tether, while still additional protective groups will be used to form the linkage between the support or any linker molecules and the tether molecule.

It will be recognized that not all protective groups will be used in all embodiments, and that in some embodiments one or more of the protective groups will be the same group. For example, in some embodiments the same protective group is used in formation of the bond between the substrate and tether as is used in the synthesis of the polymer. By way of further example, if the goal is to stop at the cyclized polymer stage, the cleavable group between the tether and the polymer becomes unnecessary. By way of still further example, side chain deprotection may be combined with the final cleavage of the linker.

Figure 1B:
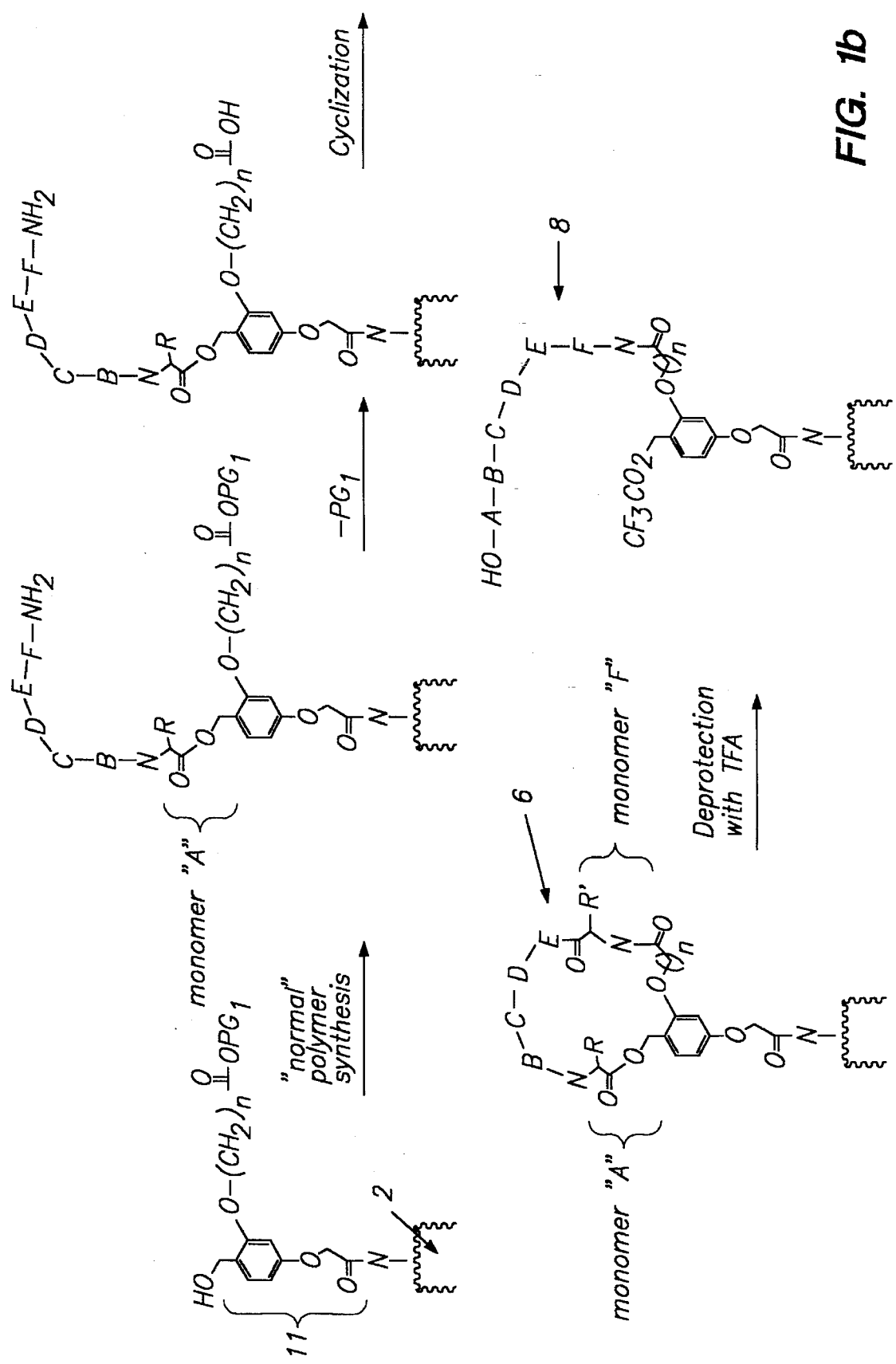

FIG. 1a provides an overall illustration of one embodiment of the invention, while FIG. 1b provides an overall illustration of the invention as applied to peptide synthesis. In FIG. 1 and elsewhere in this specification, "PG" refers to a protective group, X, Y, and Z refer to the various reactive sites discussed above, and A, B, C, D, E, and F refer to various monomers or groups of monomers.

As shown in FIGS. 1a and 1b, the process is conducted on a substrate 2. A tether molecule 4 is coupled to a surface of the substrate. The tether molecule includes one or more reactive sites such as a reactive site Z which is used to couple the tether to the substrate. In some embodiments, the tether is also provided with a reactive site X having a protective group $PG_1$ thereon. It will be recognized, however, that in other embodiments a protective group on the reactive site X is not necessary. The tether molecule further includes a reactive site Y, optionally with a protective group $PG_2$ thereon.

In a first step, a polymer synthesis is carried out on the reactive site Y. According to some embodiments, conventional polymer synthesis techniques are utilized such as those described in Merrifield, "Solid Phase Peptide Synthesis," *J. Am. Chem. Soc.*, (1963) 85:2149–2154, incorporated herein by reference for all purposes. A wide variety of techniques may be used in alternative embodiments. For example, according to one embodiment, a variety of polymers with different monomer sequences are synthesized on the substrate. Such techniques may involve the sequential addition of monomers or groups of monomers on the growing polymer chain, each monomer of which may also have a reactive site protected by a protective group.

A variety of such methods are available for synthesizing different polymers on a surface. For example, Geysen et al., "Strategies for Epitope Analysis Using Peptide Synthesis,"

J. Imm. Meth., (1987) 102:259–274, incorporated herein by reference for all purposes, describes one commonly used technique for synthesizing different peptides using a "pin" technique. Other techniques include those of Houghten et al., Nature (1991) 354:84–86, incorporated herein by reference. In some embodiments, advanced techniques for synthesizing polymer arrays are utilized such as those described in copending application Ser. No. 796,243 (now U.S. Pat. No. 5,384,261), or light-directed, spatially-addressable techniques disclosed in Pirrung et al., U.S. Pat. No. 5,143,854; and Fodor et al., "Light-Directed Spatially-Addressable Parallel Chemical Synthesis," Science (1991) 251:767–773, all incorporated herein by reference for all purposes, such techniques being referred to herein for purposes of brevity as VLSIPS™ (Very Large Scale Immobilized Polymer Synthesis) synthesis.

During polymer synthesis one may not want the activator used to remove $PG_2$ (if any) on the Y reactive site, and on reactive sites of the growing polymer chain, if any, to remove the X protective group $PG_1$. Accordingly, the protective groups (e.g., $PG_1$ and $PG_2$) typically are selected to have different and non-interfering or orthogonal deprotection protocols. Thus, one protective group (e.g., $PG_1$) can be removed under conditions which leave a second protective group (e.g., $PG_2$) substantially unaffected. Merely by way of example, the activator used to remove $PG_2$ may be a first chemical reagent, while the activator used to remove the protective group $PG_1$, may be a second, different chemical reagent. For example, in some embodiments, the first protective group is acid-labile and the second protective group is base-labile.

By way of further example, the activator used to remove one of the protective groups may be light, while the activator used to remove the other protective group may be a chemical reagent, or both activators may be light, but of different wavelengths. For example, the first protective group is an acid-labile or base-labile protective group and the second protective group is a photoreactive protective group, or vice versa. Of course, other combinations will be readily apparent to those of skill in the art on review of this disclosure.

In other embodiments, differential protective groups are used simultaneously on the ends of the growing oligomer chains (i.e., some of the oligomer chains are capped with $PG_{2a}$ and some with $PG_{2b}$, where $PG_{2a}$ and $PG_{2b}$ may be cleaved under conditions which leave the other substantially unaffected). Alternatively, differential protective groups can be used simultaneously on the second reactive site X (i.e., some of the X reactive sites are coupled to $PG_{1a}$, while others are linked to $PG_{1b}$, where $PG_{1a}$ and $PG_{1b}$ may be cleaved under conditions which leave the other substantially unaffected). This protocol allows for the production of hybrid libraries containing "normal" polarity, reversed polarity, and cyclic polymers.

One of skill in the art will also recognize that in certain embodiments, it might be necessary to utilize side chain protective groups to prevent undesired branching of the oligomer chain during synthesis and to protect sensitive side chain functionality. For example, the amino acid cysteine possesses a sulfhydryl group side chain. Sulfhydryl groups are sensitive to oxidation and also are prone to coupling to form disulfide bridges. Thus, during polymer synthesis, the sulfhydryl group will typically be protected with an appropriate protective group. When the synthetic sequence is complete, the side chain protective group can be cleaved to allow the formation of disulfide bridges to form cyclic polymers or to append heterobifunctional crosslinkers as described in copending application Ser. No. 07/972,007, filed Nov. 5, 1992.

The side chain protective groups are selected to remain in position during the synthesis of the polymer chain, and may be removed upon exposure to the same or a different activator as the activator used to cleave the Y—A bond. In a preferred embodiment, the side chain protective groups are removed only upon exposure to the same activator as the one used for cleavage of the Y—A bond, such as acid. Accordingly, during the synthesis step side chain protection is also maintained.

In some embodiments, the bond between the reactive site Y and the first monomer is cleavable upon exposure to an activator such as a selected reagent, irradiation with light, or the like. In the specific case of peptide synthesis, for example, one form of standard Merrifield peptide synthesis employs a fluorenylmethyloxycarbonyl (FMOC) on the growing end of the peptide. "Standard" techniques generally involve cycles of mild base treatment to remove the FMOC for growth of the polymer chain. According to this specific embodiment, the protective group on the reactive site X is removed not by a weak base, but by another activator such as light, fluoride ion, weak acid, strong base, a biological reagent, an ion beam, or the like. The reactive site Y is optionally cleavable from the monomer A upon exposure to still another activator such as light of a different wavelength or a strong acid.

As shown in FIGS. 1a and 1b, by virtue of proper protective group selection and exposure to only the $PG_2$ activator, the reactive site X is protected during polymer synthesis and does not take part in the initial portion of the process. Also, the reactive site Y remains bound to the tether.

As shown in the second portion of FIGS. 1a and 1b, the synthesis step of the process, which will frequently include many substeps of deprotection/coupling, results in a polymer of a desired length, schematically illustrated by the polymer "ABCDE . . . F" in FIGS. 1a and 1b. It is to be understood that a polymer with 5 or more monomers is illustrated in FIG. 1, but fewer monomers will be utilized according to some embodiments.

In a preferred embodiment, the last monomer on the polymer will be a "flexible" monomer to aid or enhance the cyclization process. Preferred flexible monomers are relatively long, as compared to other monomers of the same class, and undergo highly efficient cyclization chemistry. Examples of flexible monomers include, for example, polyethylene glycol type monomers such as 2-hydroxyethyl ether or triethylene glycol, and long chain ω-amino acids, such as 6-aminocaproic acid or 8-aminocaprylic acid. This flexible monomer becomes a new linker between the peptide and tether after cyclization and cleavage of the Y—A bond.

In a next step of the process, the protective groups $PG_1$ on the X reactive site is removed, if necessary. (It will be recognized that in some embodiments a protective group on the X reactive site is not necessary.) In addition, the reactive site on the last monomer F is rendered active, if necessary. As shown in FIGS. 1a and 1b, the reactive site on the selected monomer will then react with the reactive site X, forming a cyclic polymer 6. In a preferred embodiment for peptide synthesis, the protective group $PG_1$ is removed with light.

In a next, optional, step of the process, the substrate is treated for cleavage of the Y—A bond and, in preferred embodiments, for simultaneous removal of any side chain protective groups. Merely by way of example in one embodiment of peptide synthesis, a strong acid (up to 100% TFA) is used for both the removal of the side chain protective groups and cleavage of the Y—A bond. In another embodiment, light can be used to cleave the Y—A bond, while acid is used to deprotect the side chain protective groups.

This step of the process results in a polymer bound to the substrate, but with reversed polarity from the polarity as the polymer was originally synthesized. Thus, through the use of a conventional linkage to the support and an orthogonal group as the protective group of the second site of reactivity on the tether, reversed polarity peptides are obtained. Alternatively, any orthogonal chemically-, photochemically-, or biologically-cleavable group would work as an appropriate protective group for X.

III. Detailed Description of Preferred Embodiments

A. Protective groups

The orthogonal protection scheme of the present invention involves the simultaneous use of two or more classes of protective groups. These classes of protective groups are removed by differing chemical mechanisms, and therefore can be removed in any order and in the presence of other protective groups. Orthogonal schemes offer the possibility of substantially milder overall synthesis conditions, because selectivity can be attained on the basis of differences in chemistry rather than in reaction rates.

It will be recognized that choice of the various protective groups will be dictated by the type of polymer which is to be synthesized. Therefore, for example, oligonucleotides will often have different protective groups than will peptides, oligosaccharides, and the like. In addition, conventional solid-phase synthesis techniques without the use of photoprotective groups will utilize different protective groups than VLSIPS™ light-directed synthesis techniques. Still further, if the desired polymer is the cyclized polymer, the protective groups may be selected differently than if the final product is to be of reversed polarity. Moreover, the choice of cyclization and/or cleavage conditions will often effect the selection of protective groups. Specific examples of protective groups are discussed in detail below. Tables 1 and 2 summarize the various protective groups used according to most preferred embodiments of the invention, along with cleavable bond descriptions for polymer reversal.

TABLE 1

Protective Group Selections
Peptide Synthesis

| $PG_2$/ Activator | $PG_1$/ Activator | Cleavable Bond Activator |
|---|---|---|
| BOC/acid | FMOC/base | Acid |
| BOC/acid | FMOC/base | Light or acid |
| BOC/acid | Allyl/Pd | Acid or light |
| BOC/acid | Silyl/ Fluoride | Acid or light |
| FMOC/base | NVOC or photochem./ light | Acid |
| FMOC/base | Allyl/Pd | Acid or light |
| FMOC/base | Silyl/ Fluoride | Acid or light |
| NVOC or photochem./ light | FMOC/base | Acid |
| NVOC or photochem./ light | Allyl/Pd | Acid or light |
| NVOC or photochem./ light | Silyl/ Fluoride | Acid |

1. Conventional Peptide Synthesis

One technique of standard Merrifield peptide synthesis employs fluorenylmethyloxycarbonyl (FMOC) on the growing end (amino terminus) of the polymer and one or more of a variety of side chain protective groups. According to preferred embodiments herein, such techniques generally utilize mild base treatment to remove the FMOC ($PG_2$) for peptide growth, and strong acid (up to 100% TFA) for both removal of the side chain protective groups and cleavage of the Y—A bond.

According to some embodiments, cleavage of the tether utilizes mild acid, without removal of side chain protective groups, which are removed with a stronger acid. Base or light is used to remove the protective group $PG_2$, which may be, for example, NVOC. Other embodiments employ light for the removal of $PG_1$, acid to cleave the side chain, and base to remove the tethers. Alternatively, when light is used for the removal of $PG_1$, base can be used to cleave the side chain and acid can be employed for tether removal.

As shown herein, the method permits not only cyclization of the peptide, but also the use of conventional C terminal to N terminal synthesis techniques, while exposing the carboxyl end of the peptide after polymer reversal. In preferred embodiments, the peptide synthesis uses otherwise known peptide chemistry in which monomers are coupled to the exposed amino group during synthesis.

2. VLSIPS™ Peptide Synthesis

One embodiment of the invention utilizes a group $PG_2$ which is removable with a first wavelength of light and a second photocleavable group $PG_1$ which requires a different wavelength for deprotection of X. Preferably such groups utilize wavelengths >300 nm in order to avoid conflicting with protective groups in use during polymer synthesis and to avoid damage to sensitive amino acids. Photocleavable groups at different wavelengths are used for X—$PG_1$ and Y—$PG_2$ bond breakings. Alternatively, some embodiments employ a base- or fluoride-sensitive protective group. Other such materials include FMOC, β-cyanoethyl, t-butyldiphenylsilyl, DTS, and a plethora of others apparent to those of skill in the art. Again, a Y—A linkage resistant to acid cleavage allows access to the cyclized nucleotides.

TABLE 2

Protective Group Selections
Oligonucleotide Synthesis

| $PG_2$/ Activator | $PG_1$/ Activator | Cleavable Bond Activator |
|---|---|---|
| DMT/acid | NVOC or photochem./ light | Base |
| DMT/acid | Allyl/Pd | Light or base |
| DMT/acid | Silyl/ Fluoride | Light or base |
| NVOC or photochem./ light | DMT/acid | Base |
| NVOC or photochem./ light | Allyl/Pd | Base |
| NVOC or photochem./ light | Silyl/ Fluoride | Base |

3. Conventional Oligonucleotide Synthesis

Standard nucleotide synthesis involves the use of dimethoxytrityl (DMT) on the growing end of the polymer and a variety of protective groups on the bases and the phosphates. Monomers are added to the 5' end of the growing oligonucleotide. Mild acid is used to cleave DMT whereas either base (ammonium hydroxide) or thiophenol is used to cleave the exocyclic amine protective groups on the bases and the phosphate protective groups. Concentrated ammonium hydroxide is commonly used to cleave the polymer from the substrate.

Thus, in order to be substantially unaffected during the cleavage of $PG_2$ or the side chain protective groups, the second protective group should be inert to weak acid. In addition, ideally, the second protective group would also be capable of surviving the conditions used in tetrazole catalyzed phosphoramidate coupling and in the iodine/pyridine oxidation of phosphites to phosphates. Finally, the second protective group should be cleavable under conditions that will not compromise phosphates or nucleoside bases. Examples of second protective groups which fulfill these criteria include photocleavable protective groups, such as NV or NVOC; groups which may be removed using fluoride ion, such as SEM or TEOC (see, e.g., Lipshutz et al. (1980) *Tetrahedron Lett.* 21:3343–3346); groups which may be removed under neutral conditions (e.g., silver ion-assisted hydrolysis or palladium), such as DBMB (see Chattopadhyaya et al. (1979) *J.C.S. Chem. Comm.* 987–990) or allyl (see, e.g., Greene and Wuts, "Protective Groups in Organic Synthesis", 2nd Ed. John Wiley & Sons, Inc., New York, N.Y. (1991)); and groups which may be removed under mild reducing conditions (e.g., with sodium borohydride or hydrazine), such as LEV. Id. at 30–31, 97, and 112. For examples of photolabile protective groups for phosphate, see Baldwin et al. (1990) *Tetrahedron* 46:6879–6884.

Once again, a photocleavable group on the second site of reactivity of the tether is preferred. A Y-monomer linkage resistant to base cleavage allows access to the cyclized nucleotides. Alternatively, in some embodiments, the Y-monomer linkage is photosensitive and thus, is cleaved with light, while protective groups are removed under conditions of acid or base.

It should be recognized that NVOC, as utilized in the tables above, may refer to a broad class of groups including dimethyoxybenzyl, dimethoxydimethylbenzyl, α-methyl phenoxycinnamates, nitroveratryl, nitropiperonyl, and the like. Other groups are described in Fodor et al., PCT patent publication No. WO 92/10092 and application Ser. No. 07/624,120, filed Dec. 6, 1990, now abandoned, which is incorporated herein by reference. DMT refers to one member of a broad class of acid-sensitive protective groups, and for purposes of the present invention, any mild acid-labile protective group is equivalent to DMT.

4. VLSIPS™ Oligonucleotide Synthesis

Either two photocleavable groups $PG_1$ and $PG_2$ are utilized, or an additional orthogonal chemically- or biologically-cleavable group is utilized. A preferred embodiment uses DMT or allyl as $PG_1$.

Exemplary $PG_1$ and $PG_2$ groups for various oligonucleotide synthesis techniques are listed in Table 2, along with their activators.

5. Other Polymers

Other polymers such as oligosaccharides will use the same or different protective groups such as those described in Greene, "Protecting Groups in Organic Synthesis," including silyl (removed with fluoride ion), β-cyanoethyl (removed with base), and acetal groups (removed with acid), as well as those listed in Table 2 above.

B. Cyclization

Cyclization of the synthesized polymer back onto the tether is an important step in the process described herein, and requires attention to a number of factors. The primary factors are accessibility of the terminus of the polymer to the tether region, the efficiency of the cyclization process, the selectivity of the cyclization towards the terminal monomer unit or other desired monomer unit, the type of activation required to achieve cyclization, and importantly, the stability of the new bond formed.

There are numerous options for the type of bond formed in the cyclization process which can be generalized into two classes: those which continue the backbone motif (e.g., amide bond formation for peptides and phosphates for nucleotides) and those which employ novel linkage techniques. Cyclization may utilize, e.g., disulfides, esters, ureas, carbamates, carbonates, amides, thioesters, alkylation or acylation.

One means of cyclization provides for the use of a sulfide to disulfide conversion whereby free thiols are liberated on both the desired monomer and the tether and subsequently allowed to cyclize. Techniques by which this conversion can be affected are well known in the art. This approach would be applicable for cyclization of, for example, peptides and certain other polymers.

For the cyclization of peptides, cyclization using an amide or urea bond is also a useful ring closure reaction. This cyclization protocol involves liberation of a carboxyl group on the tether, activation via standard procedures (DCC, BOP, HBTU, etc.) and subsequent cyclization with the free terminal amino group to form an amide bond. The techniques and conditions by which these cyclic amides can be formed are well known in the art. According to one embodiment, generation of an isocyanate or thioisocyanate on the tether and intramolecular ring closure via urea or thiourea bond formation is utilized. For example, DTS can be used as a protecting group for an amino functionality. Treatment with triphenylphosphine generates an isocyanate functionality which may be exploited for ring closure.

According to this embodiment of the invention, the polymer is first synthesized on the Y reactive site. The protective group $PG_1$ is then removed which liberates the X reactive site. This reactive site is nucleophilic in nature and can attack the carbonyl carbon of the Y reactive site. (One of skill in the art of course will appreciate that the X reactive site must be sufficiently flexible to allow for it to contact the carbonyl group. Thus, in some embodiments, a flexible linker must be present between the X group and the aromatic ring.)

According to a preferred embodiment, capping of the terminal amino acid of a polypeptide with a flexible amine containing group such as 6-aminocaproic acid allows one to minimize cyclization difficulties associated with inflexible polymers. In other embodiments, the difficulties associated with inflexible polymers can be alleviated by linking the initial amino acid of a polypeptide to the substrate via a flexible amine containing group such as 6-aminocaproic acid or a polyethylene glycol type linker such as 2-hydroxyethyl ether or triethylene glycol. Alternatively, cyclization can be facilitated through the use of a flexible linker, such as polyethylene glycol type monomers (e.g., 2-hydroxyethyl ether or triethylene glycol) or long chain ω-amino acids (e.g., 6-aminocaproic acid or 8-aminocaprylic acid), to join the X reactive site to the tether molecule.

Cyclization may also occur via phosphates or ester bond formation. These options are particularly useful for nucleotide applications. Any of the conventional coupling reactions (phosphoramidite, phosphotriester, phosphodiester, phosphite triester, etc.) evident to those skilled in the art may be employed in the cyclization reaction. According to a preferred aspect of the invention, as with the peptide polymers, capping with a flexible monomer or linking the polymer to the substrate via a flexible linker may enhance the cyclization process and allow for the introduction of alternative cyclization techniques. In addition, by designing the terminal nucleotide sequence to complement the starting sequence, one may be able to enhance cyclization by taking advantage of any internal folding which effectively brings the terminal region in close proximity to the tether region.

The above techniques are illustrative of methods for cyclization reactions. Clearly other cyclization techniques apparent to those of skill in the art could be employed. These may include other photochemical, biological, chemical, or other procedures.

C. Tether Molecules

1. Peptides a) Amino Acid Tethers

As discussed above, the tether molecules (T) will generally be of the formula:

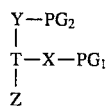

According to one embodiment, which is particularly preferred for the synthesis of cyclic peptides, the tether molecule is an amino acid with a reactive side chain. These tether molecules will typically be bound to the substrate via the carboxyl group of the amino acid. The amino group and the reactive side chain can then serve as the two reactive sites which are used for polymer synthesis and cyclization. Alternatively, the amino group of the amino acid can be employed to bind the tether to the substrate, with the side chain and carboxyl groups serving as the reactive sites.

Examples of amino acid tether molecules include, but are not limited to, serine, lysine, threonine, cysteine, aspartic acid, glutamic acid, tyrosine, 4-hydroxyproline, homocysteine, cysteinesulfinic acid, homoserine, ornithine, and the like. A particularly preferred amino acid tether molecule is glutamic acid.

b) Benzylic Tethers

According to another embodiment, which is particularly preferred for peptide synthesis with acid cleavage for polarity reversal, the tether molecule is of the benzyl group of the following general forms:

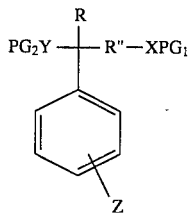

Type I

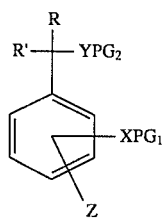

Type II

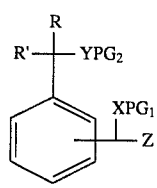

Type III

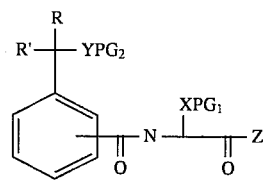

Type IV where:

R and R' are individually or both selected from the group consisting of H, methyl, alkyl (especially $C_2$ to $C_8$), aryl (including substituted phenyl, methoxy substituted phenyl), phenyl, bridged phenyl, and ring compounds, especially $C_5$ to $C_{15}$, which are formed by either 1) R and R' together with the carbon to which they are attached form a ring, or 2) either R or R' is linked to the phenyl group, thus forming a ring;

R" is a valence bond, alkyl (especially $C_2$ to $C_8$), alkoxy, aryl (including substituted phenyl, methoxy substituted phenyl), phenyl, bridged phenyl, and ring compounds, especially $C_5$ to $C_{15}$, which are formed by linking R" to the phenyl group, thus forming a ring;

X, Y are reactive sites individually selected from the group of O, NH, S, $CO_2$, S—$(CH_2)_nO$, and $NHCO(CH_2)_nCO_2$, where n is one to ten; and Z is a reactive site selected from the group of halogen (i.e., in a halo alkyl), O, NHS, S—$(CH_2)_nO$, and $NHCO(CH_2)_nCO_2$, where n is one to ten.

Figure 2:
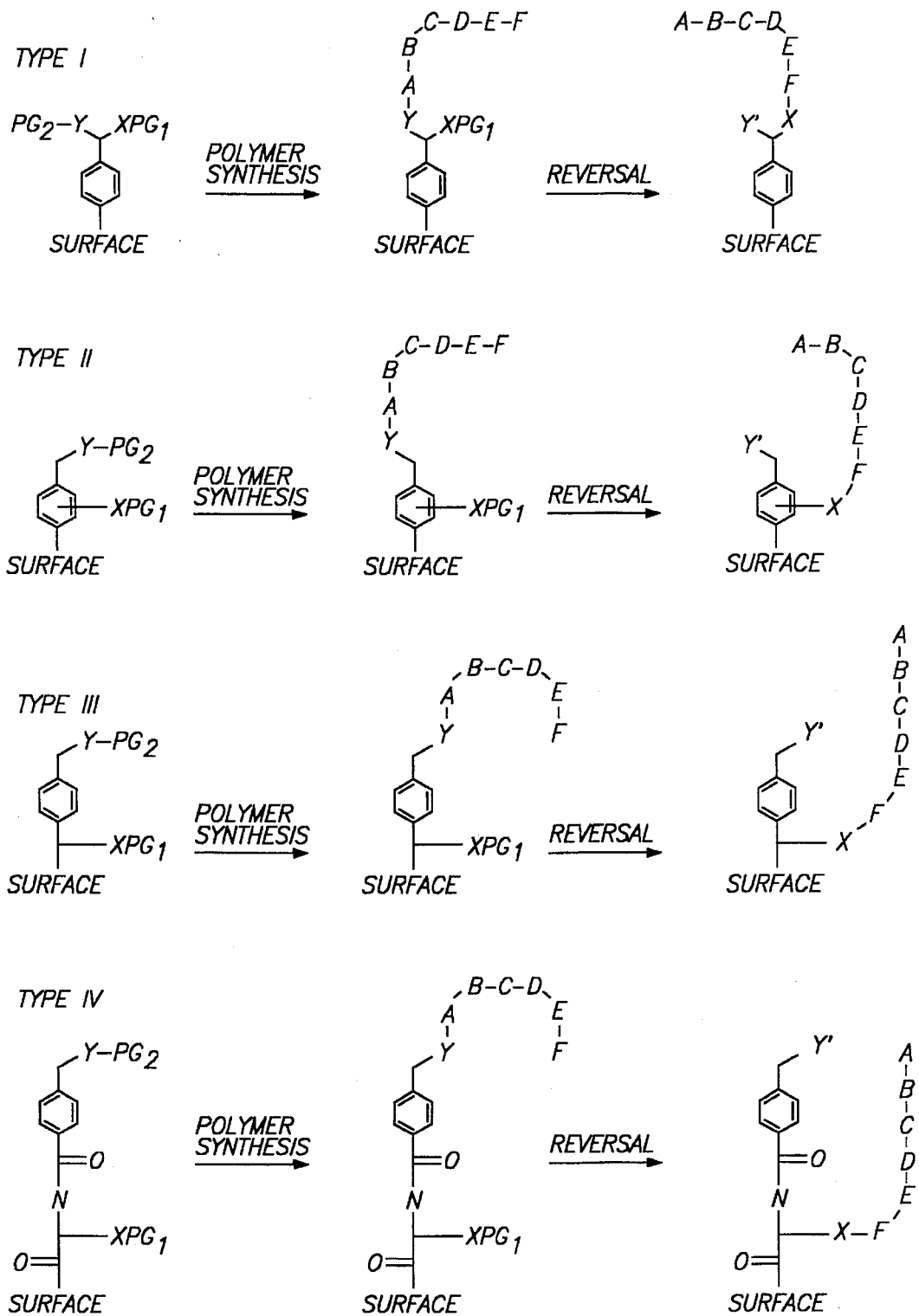
FIG. 2 illustrates the use of four types of benzylic tethers for the synthesis of reversed polarity polymers.

FIG. 2 exemplifies the use of certain of these tether molecules for the synthesis of reversed polarity polymers. Preferred examples of each of the four types of tether molecules are shown in FIG. 3. It will of course be appreciated that the figure shows the tether molecules as bound to a surface and that the unbound tether instead would possess a "Z" group in the location designated "surface" in the figure.

Type I benzylic tethers are preferred in some embodiments of this invention. For example, several known synthesis resins which may be utilized in this invention having the following general structure:

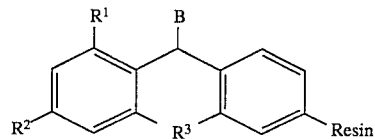

where B is O or N; $R^1$ and $R^2$ are hydrogen or methoxy; and $R^3$ is O, $CH_2$, or a valence bond. These resins can be modified using techniques well known in the art to yield a type I benzylic tether having the structure:

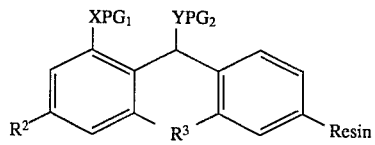

where

X, Y are reactive sites individually selected from the group of O, NH, S, $CO_2$, S—$(CH_2)_nO$, and $NHCO(CH_2)_nCO_2$, where n is one to ten; and $R^2$ and $R^3$ are as above.

Some embodiments of the instant invention employ type II benzylic tethers. Particularly preferred type II benzylic tethers are those with Y selected from the group consisting of O, NH, S, $NHCO(CH_2)_nCO_2$, and $S(CH_2)_nO$ where n is one to ten. Preferred embodiments of the invention provide for a 1-2-4 tether structure:

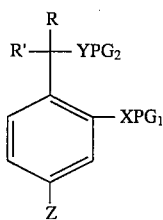

where R' and R are preferably as described above.

Alternatively, the tether may be:

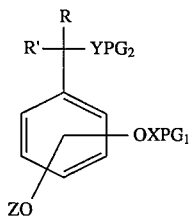

Alternatively the tether may be a 1-benzyl 4-alkoxy tether:

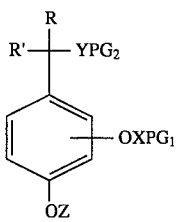

According to another preferred embodiment the tether is a 1-benzyl 2,4 dialkoxy tether:

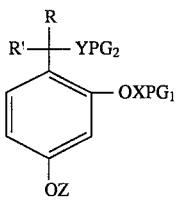

where R and R' are preferably as set forth above, and X and Z are preferably alkyl, especially $C_2$ to $C_6$ or aryl.

Most preferred groups $PG_1$ and $PG_2$ in the above compounds are:

$PG_2$: BOC, FMOC, NVOC, DMT, NV
$PG_1$: BOC, FMOC, NVOC, DMT, NV, allyl, silyl

A most preferred tether is:

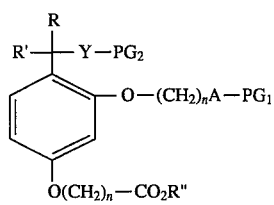

where R and R' are selected from the above-described groups; n is preferably 0 to 10; A is preferably O, N, S, CO or $CO_2$; and R" is selected from the group of H, NHS, substituted aryl.

A most preferred linker is:

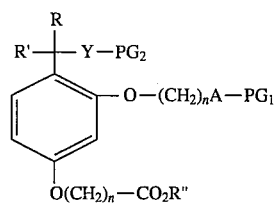

where:
the substrate binds to the acid at the para position;
R and R' are selected from the group of H, alkyl (especially $C_2$ to $C_8$), aryl (including substituted aryl), bridged ring;
A is O, N, S, CO, or $CO_2$;
n=1 to 10 and preferably about 4; and
$PG_2$ is BOC and $PG_1$ is FMOC or
$PG_1$ is NVOC and $PG_2$ is FMOC or
$PG_1$ is FMOC and $PG_2$ is NVOC or
$PG_1$ is DMT and $PG_2$ is NVOC or
$PG_1$ is NVOC and $PG_2$ is DMT or
$PG_2$ is BOC and $PG_1$ is NVOC or
$PG_2$ is NVOC and $PG_1$ is allyl. Most preferred embodiments of the invention utilize tethers of the form:

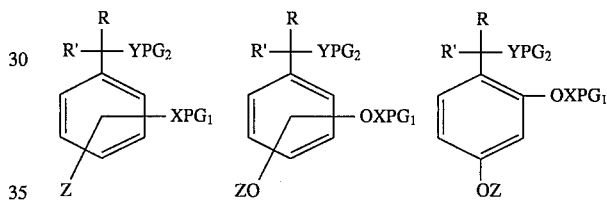

where:
Y=O, NH, S, or $CO_2$;
R, R'=H, methyl, phenyl, substituted phenyl, bridged phenyl; and
X=$(CH_2)_n APG_1$, n=0 to 10, and A=O, NH, S, $CO_2$.
Preferably:
Y=O or NH;
R, R'=H, methyl, phenyl;
X=$(CH_2)_n APG_1$, n=0 to 10, A=O, N, S, $CO_2$; and
$PG_1$=NVOC, NV, FMOC, BOC, B, DMT, allyl, silyl and
$PG_2$=FMOC, $PG_1$=NV, and A=$CO_2$ or
$PG_2$=BOC, $PG_1$=NV, and A=$CO_2$ or
$PG_2$=NVOC, $PG_1$=allyl, and A=$CO_2$ or
$PG_2$=NVOC, $PG_1$=DMT, and A=O or
$PG_2$=DMT, $PG_1$=NV, and A=O.

c) Miscellaneous Tethers

In some embodiments, the Y—T bond can be cleaved via the action of a nucleophile (i.e., a group that is capable of donating or sharing its electrons). Examples of tether molecules which would be amenable to this type of cleavage mechanism are shown below:

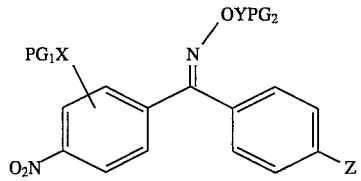

-continued

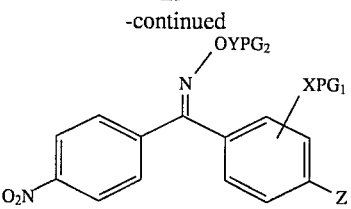

where Y is carbonyl, X is a reactive site selected from the group of O, NH, S, $CO_2$, S—$(CH_2)_nO$, and $NHCO(CH_2)_nCO_2$ and n is one to ten, and Z is a reactive site selected from the group of halogen (i.e., in a halo alkyl), O, NHS, S—$(CH_2)_nO$, and $NHCO(CH_2)_nCO_2$. Tethers of this type can be derived from commercially available resins, such as those available from AminoTech, using techniques known in the art.

According to this embodiment of the invention, the polymer is first synthesized on the Y reactive site. The protective group $PG_1$ is then removed which liberates the X reactive site. With the methods of the present invention, the X reactive site is coupled to the polymer terminus to form a cylic polymer. One of skill in the art of course will appreciate that sufficient flexibility must be present to allow the X reactive site to contact the polymer terminus. Thus, in some embodiments, a flexible linker must be utilized between the X group and the aromatic ring. Alternatively, the necessary flexibility may be obtained by appending a flexible monomer to the polymer terminus.

These tether molecules are particularly sensitive to nucleophilic attack. Treatment of the resin with a nucleophile, such as hydroxide ion, ammonia, or hydrazine, affords cleavage of the Y reactive site from the polymer and hence, formation of the reversed polarity polymer, and regenerates the oxime moiety of the resin.

2. Oligonucleotides

As discussed above, the tether molecules (T) will generally be of the formula:

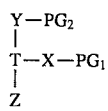

The benzylic compounds discussed above are also useful in the reversal of nucleotide polymers, except that the linkage between the aryl group and the reactive group Y need not be a benzylic linkage, because one can link Y directly to the aryl ring.

According to another specific embodiment, especially preferred for oligonucleotide synthesis, an aromatic tether (not limited to benzyl) is utilized of the general form:

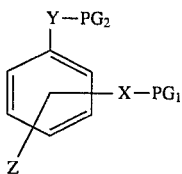

where:

X, Y are reactive sites individually selected from the group of O, NH, S, $CO_2$, S—$(CH_2)_nO$, and $NHCO(CH_2)_nCO_2$ where n is one to ten; and Z is a reactive site selected from the group of halogen, OH, NHS, S—$(CH_2)_nOH$, $NHCO(CH_2)_nCO_2H$, carboxyl, $(CH_2)_nCO_2H$, wherein n is one to ten.

Novel oligonucleotide tethers provided herein also include:

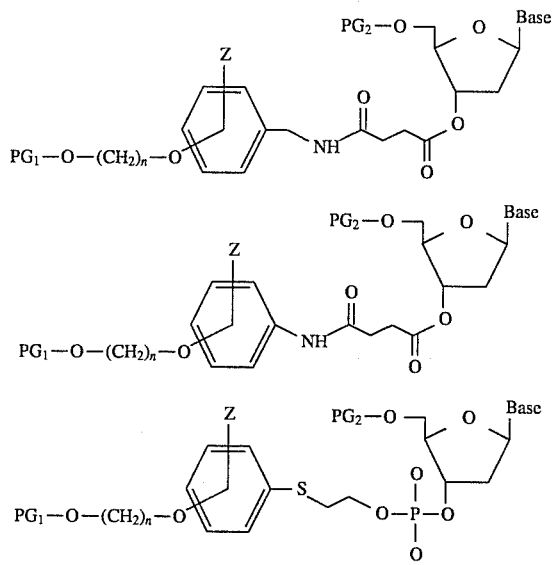

where $PG_1$ and $PG_2$ are first and second protective groups, respectively and n is one to ten; and Base is cytosine, thymine, uracil, adenine, guanine, hypoxanthine, xanthine, or inosine.

IV. Use of the Synthesized Polymers

The polymers synthesized according to the invention herein will have a variety of uses. Among the uses of the cyclic and polarity reversed polymers will be screening of the polymers for binding with a receptor, nucleotide sequencing, and the like. Screening of peptides, for example, to determine their affinity with a receptor is discussed in detail in PCT application No. WO 90/15070, previously incorporated by reference herein. Sequencing may also use the method disclosed in U.S. Pat. No. 5,064,767, previously incorporated herein by reference.

Some embodiments will employ a library of polarity reversed polymers, while other embodiments will utilize a library of cyclized polymers for screening. In addition, using the techniques of the present invention, hybrid libraries which simultaneously contain polymers of "normal" polarity, polarity reversed polymers, and cyclized polymers can be produced.

V. Examples.

A. Tether Attachment - Overall Description

The most prevalent method of anchoring a growing peptide to a solid support relies on an acid-cleavable benzylic bond as the critical bond undergoing cleavage. There are many common resins which differ as to their compatibility to the standard protection protocols (BOC versus FMOC) and as to whether an amide or free acid is desired on the C terminus. These are described in commercial supply catalogs such as those by Amino-Tech.

There are several common types of linkers for anchoring a growing oligonucleotide to a solid support, as depicted in FIGS. 4a to 4c such as polystyrene (FIG. 4a), controlled pore glass (FIG. 4b), and a CAMET linkage (FIG. 4c).

B. Examples

1. Synthesis of a Type I Benzylic Tether

Figure 5:
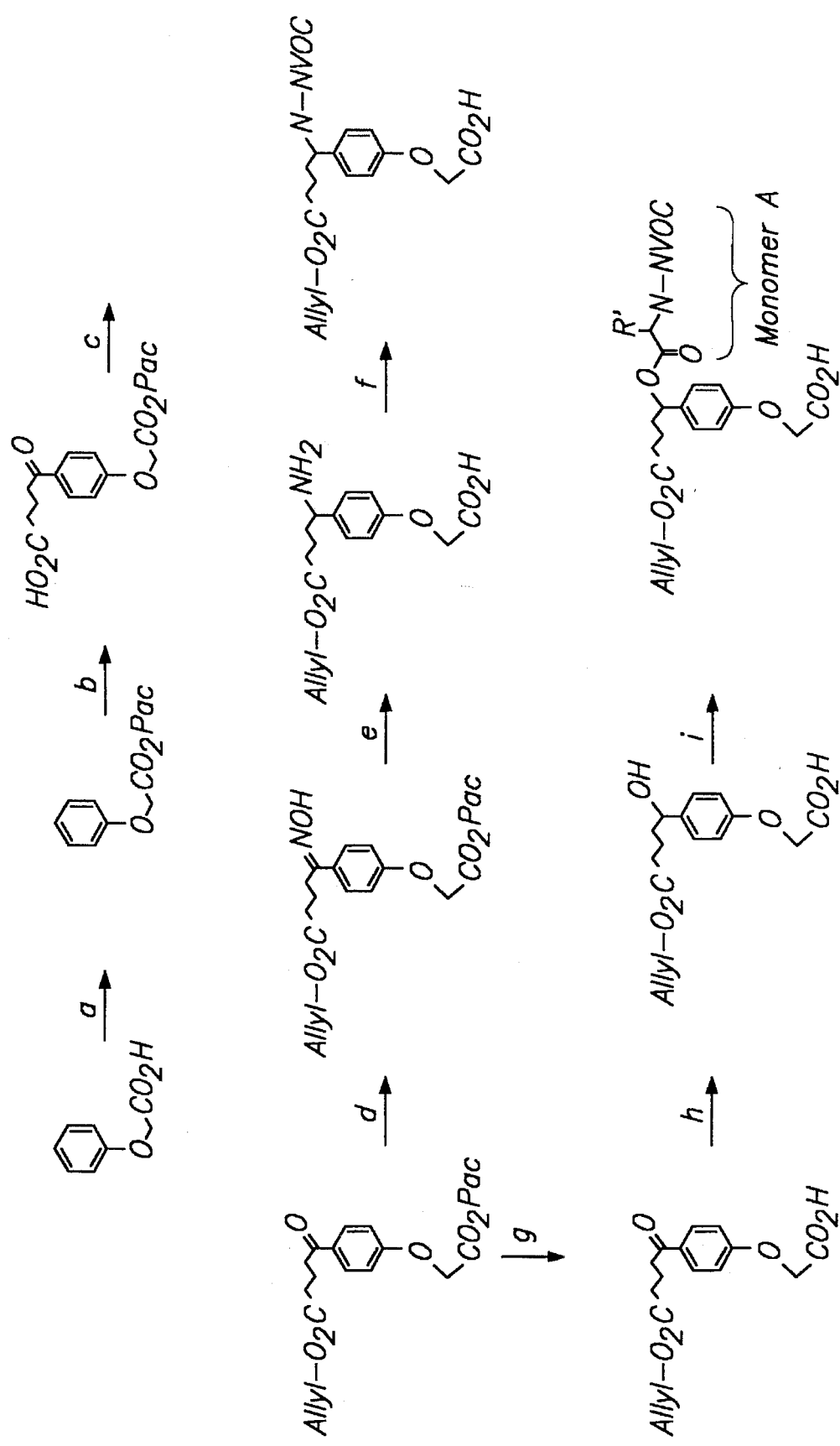
FIG. 5 provides an exemplary process for the synthesis of type I benzylic tethers.

FIG. 5 illustrates a specific process which is proposed for use in accordance with the invention.

Phenoxyacetic acid is utilized as the starting material according to this process for the synthesis of type I benzylic tethers. The carboxyl group is first protected with a suitable protective group. One embodiment provides for its protection as the Pac ester. The Pac ester is formed via the reaction of the carboxylic acid, α-bromoacetophenone and an acid scavenger, such as triethylamine. Other protective groups which may be utilized include a variety of silyl protective groups, such as 2-trimethylsilylethoxy.

A Friedel-Crafts acylation is then conducted using glutaric anhydride and aluminum trichloride. One of skill in the art will appreciate that a variety of acylation techniques and reagents can be employed which will yield similar results. The resulting carboxylic acid is then protected with $PG_1$. In some embodiments, $PG_1$ will be allyl and may be introduced via the reaction of allyl bromide and potassium carbonate or other base.

The ketone moiety is then converted to its oxime derivative through the action of hydroxylamine and pyridine. The Pac protective group is removed and the oxime is reduced to the corresponding amine using zinc and acetic acid. Again, one of skill in the art will appreciate that a variety of techniques and reaction conditions can be utilized for the reductive amination of the ketone group. In addition, the deprotection conditions of the carboxylic acid will vary with the choice of protective groups. Thus, although the above description calls for concurrent deprotection and reductive amination, depending on the choice of techniques for each transformation, the deprotection and reductive amination steps need not occur concurrently.

The amino group is protected with the protective group $PG_2$. In some embodiments, $PG_2$ will be NVOC and can be introduced through the action of NVOC-Cl and a base, such as sodium bicarbonate. This procedure thus yields a type I benzylic tether with NVOC as $PG_2$ and allyl as $PG_1$.

Another type I benzylic tether can be obtained through modification of the allyl-Pac-protected dicarboxylic acid described above. The Pac group is first removed with zinc and acetic acid or hydrogen and palladium on carbon to yield the carboxylic acid. The ketone moiety is reduced using techniques well known in the art, for example, sodium borohydride. The resulting hydroxyl group is then coupled to a monomer which has been protected with $PG_2$ to yield a type I benzylic tether with a variety of $PG_2$ groups and allyl as $PG_1$.

2. Synthesis of a Type II Benzylic Tethers

FIG. 6 illustrates a process for the synthesis of a type II benzylic tether and its attachment to a substrate. A compound of formula 10 is utilized as a starting material, where R and R' are individually selected from the group of —OH, —$NH_2$, —SH, halogen, and —$CO_2R"$; and R" is selected from the group of H, alkyl (esp. $C_2$ to $C_8$), alkylaryl, and aryl. Such para-hydroxy compounds are described in, for example, Wymann et al., 1988 *Symp. Commun.* (1988) 18:1379–1381.

Alkylation of a compound of formula 10 can be achieved through standard techniques known in the art. For example, a compound of formula 10, where R and R' are individually selected from the group of —OH, —$NH_2$, —SH, or —$CO_2H$, can be contacted first with a strong base to effect removal of the acidic hydrogen. Suitable bases include alkali metal hydroxides (e.g., sodium hydroxide), alkali metal alkoxides (e.g., potassium methoxide), alkali metal hydrides (e.g., sodium hydride), alkali metal di(lower alkyl)amines (e.g., lithium di(isopropyl)amine), and the like. The reaction mixture is then contacted with a solution of X—$(CH_2)_n$—$PG_1$, where X is halogen and n is 1 to 10, to yield a compound of formula 12, where A is O, NH, S, $CO_2$, or the like, depending upon the reactant used. Alternatively, a solution of X—$(CH_2)_n$—$PG_1$, where X is —OH, —$NH_2$, —SH, or —$CO_2H$ and n is 1 to 10, can be contacted with a strong base and then with a compound of formula 10 where R is halogen, to yield a compound of formula 12.

The compound of formula 12 can be converted to a compound of formula 14, where B is selected from the group of —OH, —$NH_2$, —SH, or halogen. These conversions again can be affected through techniques well known in the art. For example, the ketone group of a compound of formula 12 can be converted to an amino group via reductive amination with hydroxylamine, followed by treatment with zinc in acetic acid. Alternatively, to produce a compound of formula 14, where B is —OH, the compound of formula 12 can be contacted with a reducing agent, such as sodium borohydride. See, e.g., March, *Advanced Organic Chemistry*, 3rd Ed., John Wiley & Sons, New York (1985), 1146.

The compound of formula 14 is then contacted with a solution of a compound having the formula:

X-monomer-$PG_2$ where X is halogen, —OH, —$NH_2$, —SH, or the like, to form a compound of formula 16. One of skill in the art will appreciate that the coupling method will vary with the types of X and B groups. The compound of formula 16 is then exposed to a surface of a substrate 2 for binding thereto.

3. Specific Embodiments a) First Specific Embodiment

Figure 7:
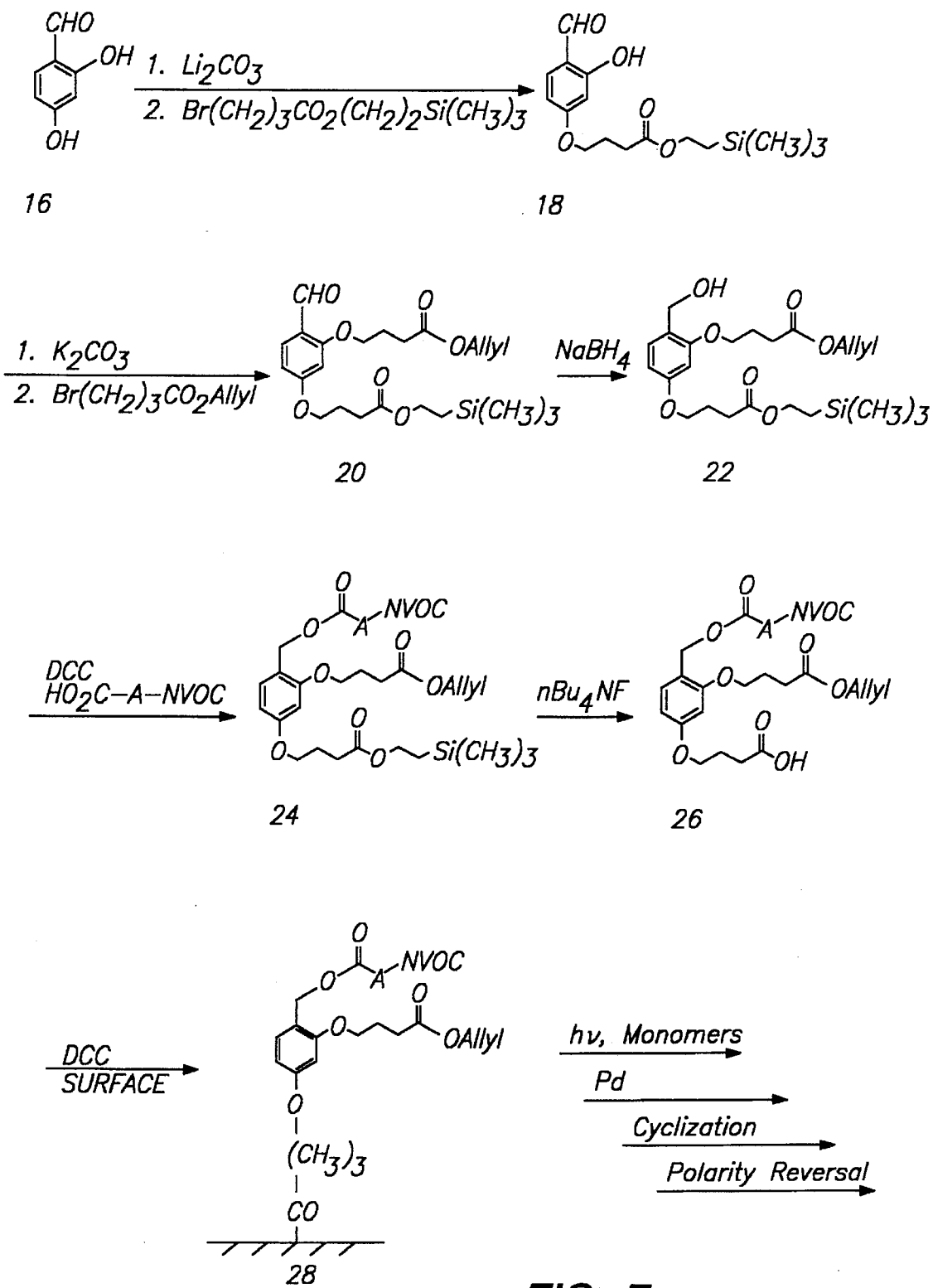
FIG. 7 illustrates a preferred process for tether attachment and use.

FIG. 7 illustrates a specific process which is proposed for use in accordance with the invention.

To a solution of lithium carbonate (25 millimoles (mmol)) and 2-trimethylsilylethyl 4-bromobutyrate (10 mmol) in DMF, is added a compound of formula 16 (10 mmol). The solution is stirred at 80° C. for about 24 hours to yield a compound of formula 18, which can be isolated and purified by conventional means.

To a solution of potassium carbonate (25 mmol) and allyl 4-bromo-butyrate (10 mmol) in DMF is added a compound of formula 18 (10 mmol). The reaction mixture is stirred at about 80° C. for about 24 hours. The product, a compound of formula 20, can be isolated and purified by conventional means.

To a solution of a compound of formula 20 (10 mmol) in ethanol, is added sodium borohydride (10 mmol). The reaction solution is stirred at room temperature for about 24 hours. The product, a compound of formula 22, can be isolated and purified by conventional means.

To a solution of a compound of formula 22 (10 mmol) in DMF, is added DCC (10 mmol) and $HO_2C$-A-NVOC (10 mmol), where A is the first monomer terminating in O, NH, or S. The reaction mixture is stirred at room temperature for about 24 hours. The product, a compound of formula 24, can be isolated and purified by conventional means.

The compound of formula 24 is then treated with excess tetrabutylammonium fluoride to remove the trimethylsilylethoxy group. The product, a compound of formula 26, can be isolated and purified by conventional means.

The compound of formula 26 is then contacted with a surface of the substrate in a DCC solution, to provide a surface-attached compound 28. The surface is treated with light to couple additional monomers, in accordance with the procedures described in the copending applications incorporated by reference above. Cyclization is accomplished by exposing the completed substrate to tetrakis(triphenylphosphine)palladium, followed by treatment with an activator, such as BOP or DPPA. Polymer reversal is accomplished by exposing the substrate to a strong acid (about 1 to 100% TFA).

b. Second Specific Embodiment

Figure 8:
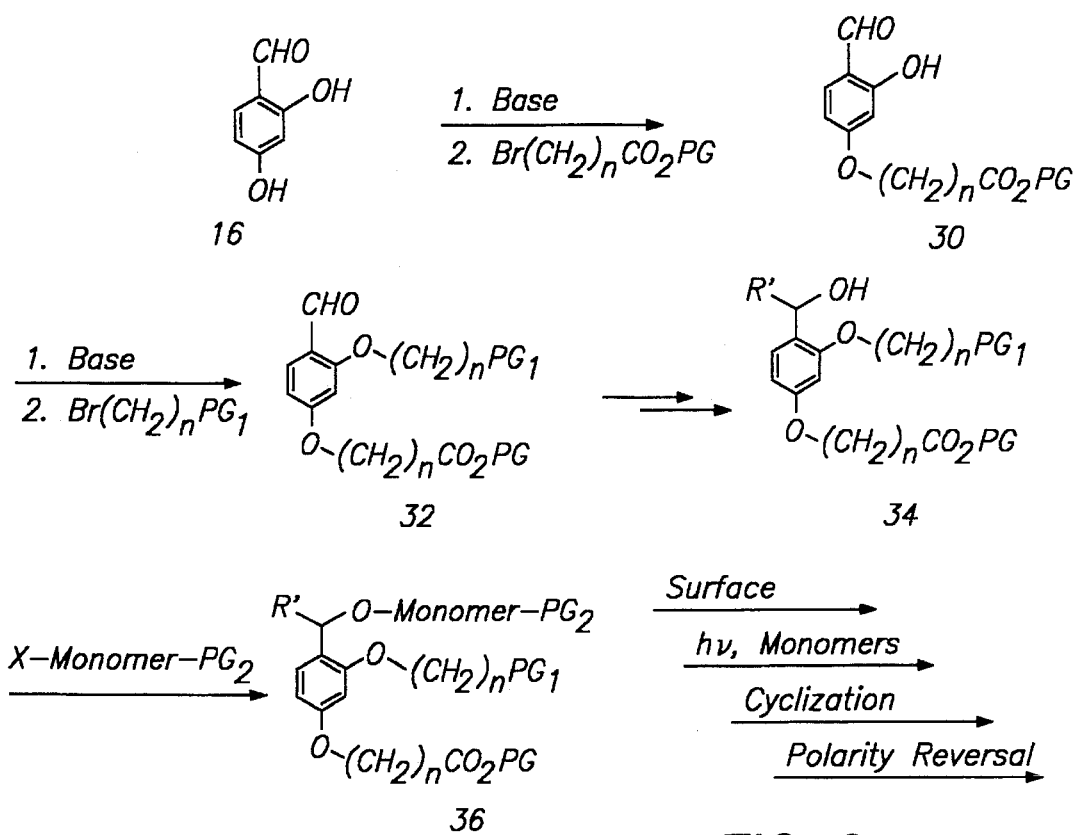
FIG. 8 illustrates a preferred process for tether attachment and use.

FIG. 8 illustrates another specific embodiment of the invention. To a solution of lithium carbonate (25 millimoles (mmol)) and Br—$(CH_2)_n$—$CO_2PG$ (where n is about 2 to 8, and PG is selected from the group of alkyl ($C_2$ to $C_8$), trimethylsilylethyl, and NHS; 10 mmol) in DMF, is added a compound of formula 16 (10 millimoles) (mmol). The solution is stirred at 80° C. for about 24 hours to yield a compound of formula 30, which can be isolated and purified by conventional means.

To a solution of potassium carbonate (25 mmol) and Br—$(CH_2)_n$—$PG_1$ (n=2 to 8; 10 mmol) in DMF is added a compound of formula 30 (10 mmol). The reaction mixture is stirred at about 80° C. for about 24 hours. The product, a compound of formula 32, can be isolated and purified by conventional means.

The compound of formula 32 is then reduced using techniques well known in the art to produce a compound of formula 34, where R' is selected from the group of H, Me, alkyl ($C_2$ to $C_8$), substituted phenyl, and phenyl. See, e.g., March at 1146.

To a solution of a compound of formula 34 (10 mmol) in DMF, is added DCC (10 mmol) and a solution of X-monomer-$PG_2$ (10 mmol) in DMF. The reaction mixture is stirred at room temperature for about 24 hours. The product, a compound of formula 36, can be isolated and purified by conventional means. This compound is then contacted with a surface of the substrate in a DCC solution, to provide a surface-attached compound. The compound may then be subjected to additional monomer reactions, cyclization and, optionally, polymer reversal in accordance with the above description.

c. Third Specific Embodiment

Figure 9:
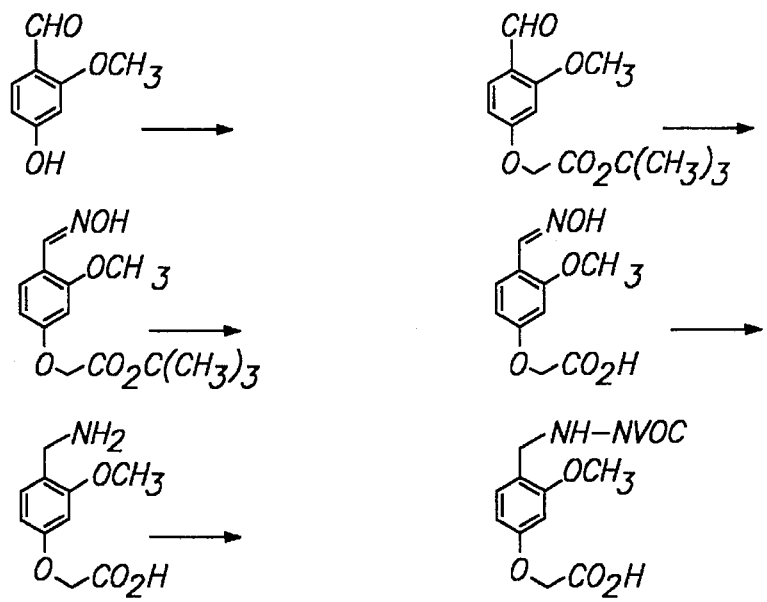
FIG. 9 provides an exemplary process for the synthesis of type II benzylic tethers.
Figure 10A:
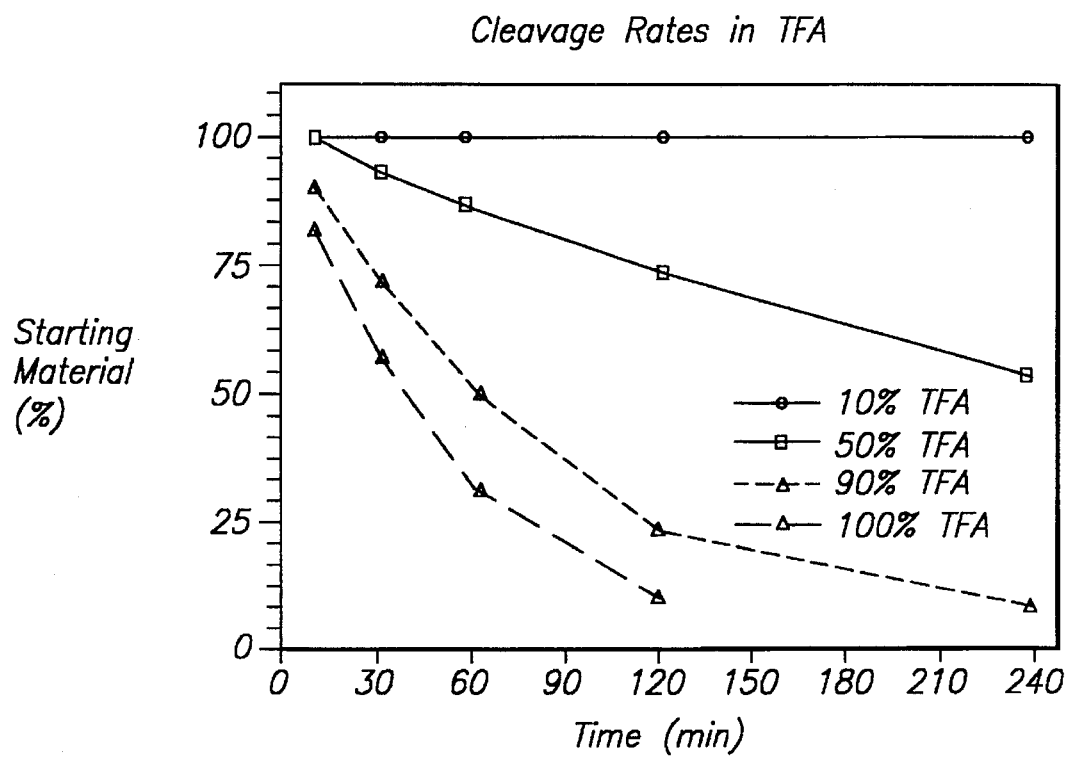
FIG. 10a–10d are a graphical representations of the cleavage rates NVOC-cleavable linkers using different concentrations of trifluoroacetic acid.
Figure 10B:
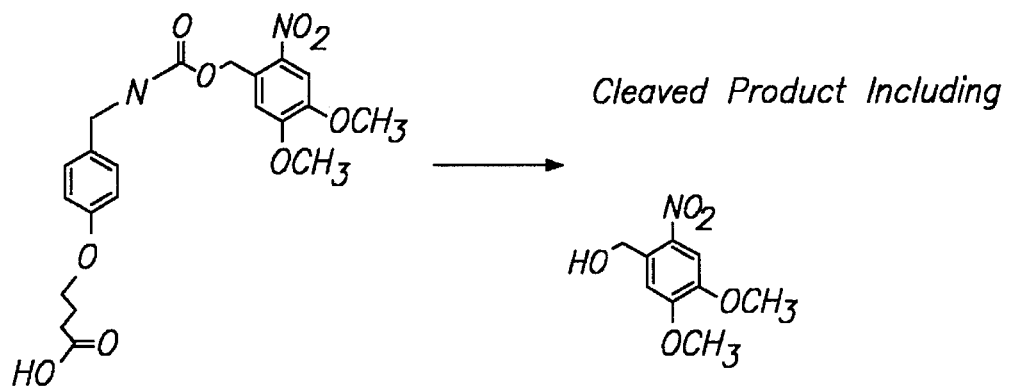
Figure 10C:
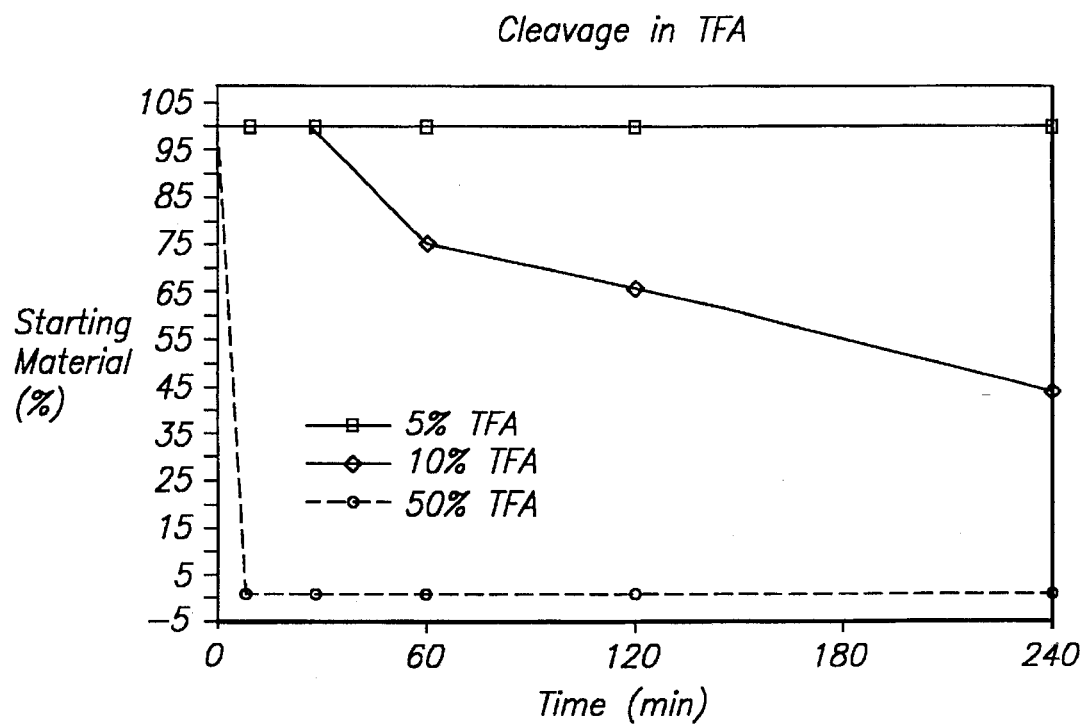
Figure 10D:
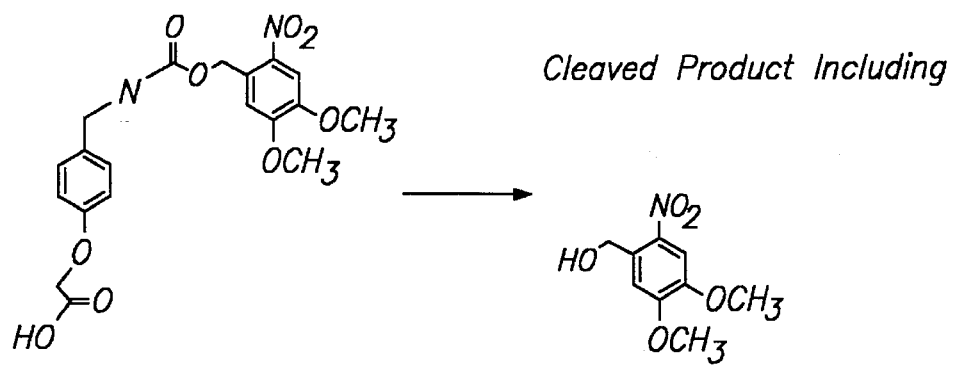

FIG. 9 illustrates another specific embodiment of the invention.

A mixture of 4-hydroxy-2-methoxybenzaldehyde (5.23 g; 34.4 mmol), t-butyl bromoacetate (4.9 mL; 30.3 mmol) and $K_2CO_3$ (15.1 g; 108.9 mmol) in 50 mL of DMF was stirred at room temperature for 16 hours. The reaction mixture was diluted with ethyl acetate, filtered, and partitioned between ethyl acetate and 1 N HCl. The organic phase was washed (sat. NaCl) and dried ($MgSO_4$), and concentrated to give 17.59 g of t-butyl 4-formyl-3-methoxyphenoxyacetate as a white solid.

A solution of t-butyl 4-formyl-3-methoxyphenoxyacetate (7.59 g; 28.5 mmol) in 20 mL of ethanol and 200 mL of 2:1 pyridine:water was treated with $H_2NOH\cdot HCl$ (4.16 g; 60.0 mmol) for 20 hours at room temperature. The solvent was evaporated and the residue was stirred for 3 hours with 150 mL of 10% acetic acid in water. The precipitate was collected to give 8.81 g of crude oxime. The oxime was stirred in 50% TFA/$CH_2Cl_2$ for 4.5 hours and the reaction mixture was partitioned between $CH_2Cl_2$ and $H_2O$. Evaporation of the solvent afforded approximately 7 g of a white solid. The crude oxime-acid was dissolved in 300 mL of methanol and hydrogenated with 10% Pd/C (1.2 g) under an 1.1 atm pressure of hydrogen. After stirring for 20 hours at room temperature, the catalyst was filtered off and the solvent evaporated to give 4.74 g of the crude amino acid as a semi-solid. A solution of NVOC-Cl (6.29 g; 22.8 mmol) in 30 mL of dioxane was added to a solution of a mixture of the amino acid (4.74 g; 22.4 mmol), $NaHCO_3$ (1.94 g; 23.1 mmol), and NaOH (0.96 g; 24.1 mmol) in 50 mL of $H_2O$ and 20 mL of dioxane. The solution was stirred for 19 hours and then partitioned between $H_2O$ and ethyl acetate. The organic phase was discarded and the aqueous phase was acidified with 3 N HCl and was extracted with ethyl acetate. The organic phase was washed (sat. NaCl), dried ($MgSO_4$), and evaporated to give 5.30 g (52% yield) of the NVOC-cleavable linker as a light yellow solid.

d. Fourth Specific Embodiment

TFA Cleavage of Linkers

A 50 mM stock solution of each NVOC-cleavable linker in DMSO was prepared and 100 μL was added to 5 mL of various concentrations of TFA in $CH_2Cl_2$ (0, 10, 50, 90, 100%). Aliquots (200 μL) were withdrawn at the designated time intervals and diluted with 500 μL of 1:1 acetonitrile:$H_2O$ to quench the reaction and then further diluted with 1 mL of acetonitrile. Analysis of the samples via HPLC (C18 reverse phase with uv detection) revealed the extent of reaction. The presence of a single electron donating substituent (4-hydroxybutyrate) on the aromatic ring affords a linker which can be cleaved within a short time. The presence of a second electron donating substituent (methoxy) affords a linker even more susceptible to cleavage with TFA. The linkers were also shown to be stable to incubation for 24 hours with 5 mM $H_2SO_4$ in dioxane.

For dialkoxy methyl groups, about less than 100% and preferably about 20–50% TFA is used for cleavage, preferably for less than 5 hours and more preferably about 1–2 hours. For trialkoxy methyl groups, less than about 10% TFA can be used for cleavage. These results are shown graphically in FIGS. 10a–10d.

C. Cyclization

1. First Specific Embodiment a) Synthesis of an Amino Acid Tether

Figure 11:
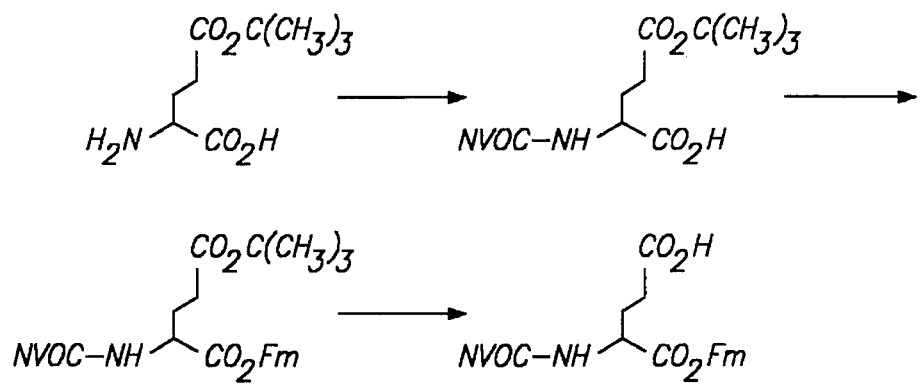
FIG. 11 provides a preferred process for the synthesis of amino acid tethers.

FIG. 11 illustrates a specific process which is proposed for use in accordance with the invention.

A solution of NVOC-Cl (3.90 g; 14.1 mmol) in 35 mL of dioxane was added to a solution of H—Glu(OtBu)—OH (2.00 g; 9.42 mmol) and $NaHCO_3$ (1.60 g; 19.0 mmol) in 25 mL of dioxane and 10 mL of $H_2O$ at room temperature. After stirring for 1 hour, the reaction mixture was partitioned between diethyl ether and sat. $NaHCO_3$. The organic phase was discarded and the aqueous phase was acidified to pH 2 with 3 N HCl and extracted with ethyl acetate. The organic phase was dried ($MgSO_4$) and evaporated to afford 3.58 g (86% yield) of NVOC-Glu(OtBu)—OH as a light yellow solid.

A solution of NVOC—Glu(OtBu)—OH (1.00 g; 2.25 mmol), 9-fluorenemethanol (485 mg; 2.47 mmol), and 4-dimethylaminopyridine (41 mg; 0.34 mmol) in 20 mL of $CH_2Cl_2$ was treated with DCC (470 mg; 2.28 mmol) for 25 minutes at room temperature. The reaction mixture was filtered and the filtrate was partitioned between $CH_2Cl_2$ and 1 N HCl. The organic phase was washed (sat. $NaHCO_3$), dried ($MgSO_4$), and evaporated to yield a white slurry. Chromatography on silica gel (10% $CHCl_3$, 20% ethyl acetate, 70% hexanes to 50% ethyl acetate, 50% hexanes) afforded 1.21 g (87% yield) of NVOC—Glu(OtBu)—OFm as a light yellow solid.

A solution of NVOC—Glu(OtBu)—OFm (1.04 g; 1.67 mmol) in 35 mL of $CH_2Cl_2$ was treated with 6 mL of TFA for 1.5 hours at room temperature. The reaction mixture was partitioned between ethyl acetate and 1 N HCl and the organic phase was dried ($MgSO_4$) and evaporated to give 1.00 g of a light yellow solid. Recrystalization from methanol/$H_2O$ gave 0.76 g (81% yield) of NVOC—Glu—OFm as an off-white powder.

b) Cyclization

Eight slides derivatized with NVOC-aminocaproic acid were photodeprotected for ten minutes in 5 mM sulfuric acid/dioxane using 365 nm light. After neutralization of the surface, six of the slides were exposed to 0.1 M BOP activated NVOC—Glu(O-t-butyl)—OH, while the remaining two slides were exposed to 0.1 M BOP activated NVOC—Glu—OFm. The first six slides were divided into three groups and each group was derivatized with either BOP activated Boc-Pro-Pro-Pro-Pro-OH (SEQ ID NO:1), Boc-Ala-Ala-Ala-Ala-OH (SEQ ID NO:2), or Boc-Ala-Gly-Gly-Gly-OH (SEQ ID NO:3). The second two slides from above were derivatized with BOP activated Boc-Val-Val-Val-Val-OH (SEQ ID NO:4). This gave four pairs of slides, each with a pentapeptide Pro-Pro-Pro-Pro-Glu (SEQ ID NO:5); Ala-Ala-Ala-Ala-Glu (SEQ ID NO:6); Ala-Gly-Gly-Gly-Glu (SEQ ID NO: 7); and Val-Val-Val-Val-Glu (SEQ ID NO:8) on the surface with a side chain carboxyl (still protected) with which to cyclize. All eight slides was deprotected with 50% TFA in $CH_2Cl_2$ to remove the Boc and t-butyl groups (from both the amino terminus and the masked carboxyl group), and then the two slides with Fm as protecting group were treated with 30% piperidine in $CH_2Cl_2$ to unmask the carboxyl group.

A sixteen-well template was placed on each slide in order to physically segregate different regions of the surface and one member of each pair was warmed (either 41° or 44° C.) while the second member was kept at 20° C. during the following reactions. Each well of the template was treated with either a 0.1 M solution of activator or just solvent for 4.5 hours. The activators were BOP (benzotriazol-1yloxy-tris(dimethylamino)phosphonium hexafluorophosphate), HBTU (O-benzotriazol-1yl-N,N,N'N'-tetramethyluronium hexafluorophosphate), and DPPA (diphenylphosphoryl azide). After the specified time, the wells were washed and the templates removed and the slides were incubated with a 10 mM solution of a 9:1 mixture of PITC (phenyl isothiocyanate):FITC (fluorescein isothiocyanate). The slides were washed and scanned for fluorescence as described elsewhere.

Figure 12:
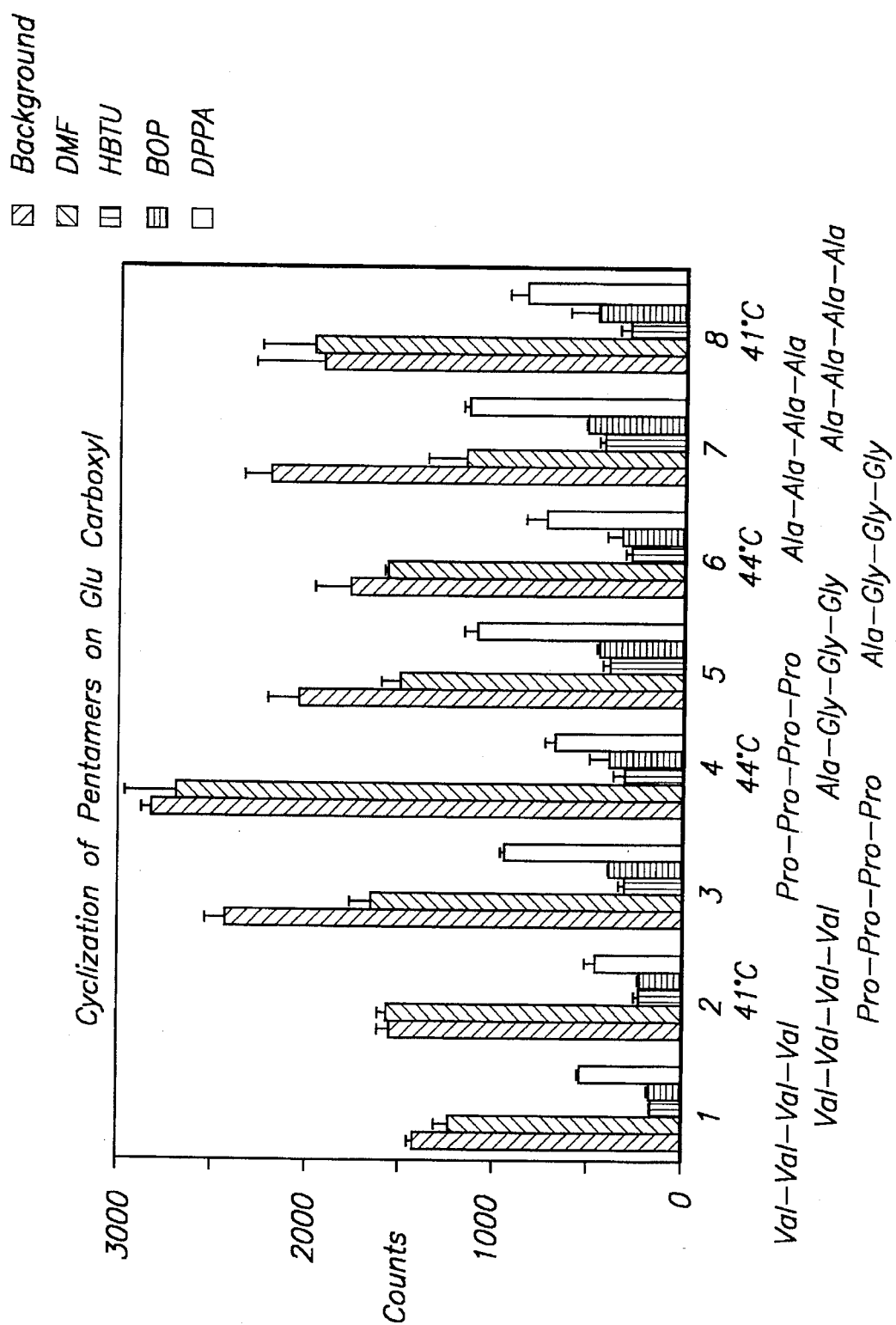
FIG. 12 (SEQ ID NOS: 8, 5, 7, 6) is a graphical representation of the cyclization efficiency, as measured by fluorescence intensity, for a variety of polypeptides and activators.

Cyclization of the peptides was expected to result in the loss of reactivity of the terminal amine, and hence, the loss of fluorescence intensity. Cyclization efficiency was measured as the decrease in fluorescence intensity for the peptides that had been treated with an activator as compared to untreated peptides. As shown in FIG. 12, cyclization was found to occur readily for all pentapeptides. The lowest signals represent regions were cyclization has occurred. Background represents regions not exposed to either solvent or activator. The activators BOP and HBTU were found to be more effective than DPPA. Temperature had little effect on the cyclization efficiency.

2. Second Specific Embodiment

A Boc-aminopropyl silane slide was deprotected with 50% TFA in $CH_2Cl_2$ for 30 minutes. After neutralization for 10 min by immersion in 10% diisopropylethylamine/$CH_2Cl_2$, the slide was derivatized with a 0.1 solution of BOP-activated NVOC—Glu(OtBu)—OH in DMF for 2.5 hours at room temperature. The slide was washed (DMF, ethanol, $H_2O$, ethanol) and air dried. The slide was immersed in 5 mM $H_2SO_4$ in dioxane and photolyzed with the 350–450 nm output from a Hg(Xe) ARC lamp at a power of 10.5 mW/cm². The slide was neutralized by immersing in 10% diisopropylethylamine/$CH_2Cl_2$ for 10 minutes, and was then derivatized with a 10 mM solution of BOP-activated Boc-Tyr-Gly-Gly-Phe-Leu-OH (amino acids 1–5 of SEQ ID NO:9) (leu-enkephalin) in DMF for 3.5 hours at room temperature. The excess reagent was rinsed off the slide with DMF, $H_2O$ and ethanol and the slide was air dried. The terminal Boc was removed by immersing the slide in 50% TFA in $CH_2Cl_2$ for 30 minutes at room temperature and then neutralized as before and washed.

A 16-well template was placed on the slide to physically segregate different regions of the surface and the entire slide was warmed to 43°–44° C. by placing it in contact with a commercially available aluminum heating block (VWR Scientific). The wells were then filled (65 μL) with either a 0.1 M solution of HBTU (also 0.1 M in HOBt and 0.37 M diisopropylethylamine) in DMF or solvent alone as control. The wells were incubated for 5 hours and then were washed with DMF, ethanol, and $H_2O$.

Incubation of the surface immobilized peptides with various regents was performed at room temperature with the template in place. The wells were exposed to either of two reagents: (1) 1 mM FITC/9 mM PITC (Fluorescein- and phenyl-isothiocyanate) in DMF for 2 hours, or (2), 10 μg/μL anti-leu-enkephalin antibody (mouse) for 2 hours followed by 10 μg/μL anti-mouse-FITC conjugate (Vector Labs) for 2 hours. The wells were rinsed with $H_2O$ and ethanol, and the template was removed and the slide further washed as before. Detection of fluorescence was performed as described elsewhere using the 488 nm emission from a Argon laser.

Figure 13:
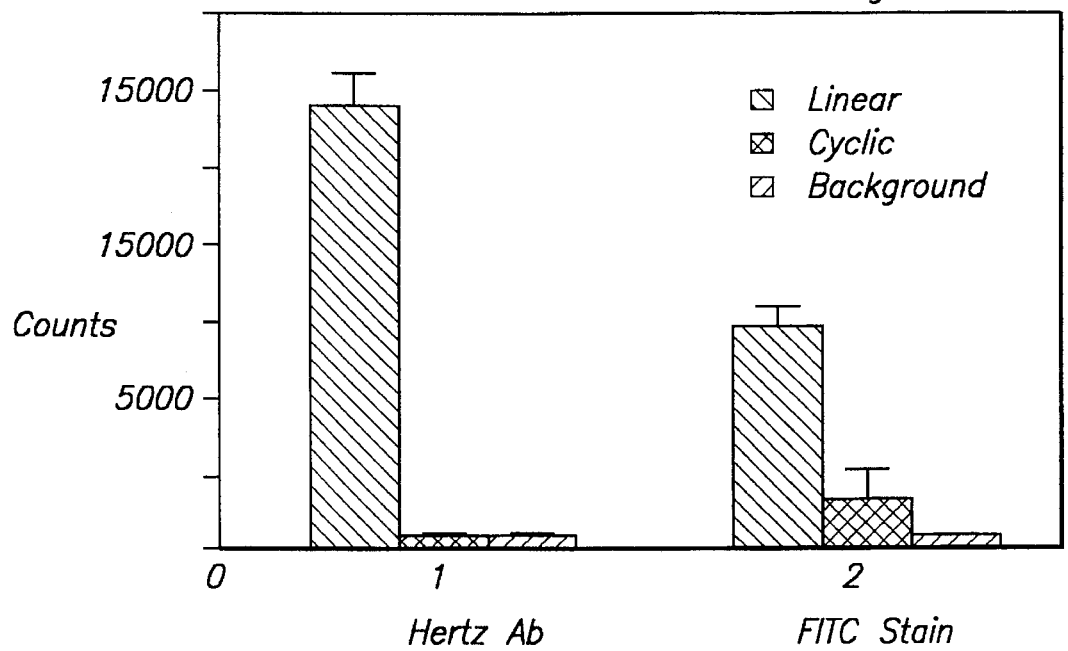
FIG. 13 is a graphical representation of the cyclization efficiency, as measured by fluorescence intensity, for the cyclization of Tyr-Gly-Gly-Phe-Leu-Glu-(SEQ ID No. 9)

The observed fluorescence signals are shown in bar graph form ("linear" refers to the solvent-alone control, "cyclic" refers to the cyclized peptides, and "background" refers to background fluorescence) in FIG. 13. As expected, the presence of cyclization reagent promoted the cyclization of the terminal amine group onto the side chain carboxyl of Glu, and hence rendered the terminal amine unavailable for binding to either the FITC or antibody reagents. The anti-leu-enkephalin antibody (also known as Hertz antibody) is known to be unable to bind leu-enkephalin when an additional amino acid has been coupled onto the terminal amine.

D. Polymer Reversal

1. First Specific Embodiment

Figure 14A:
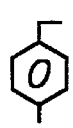
Figure 15A:
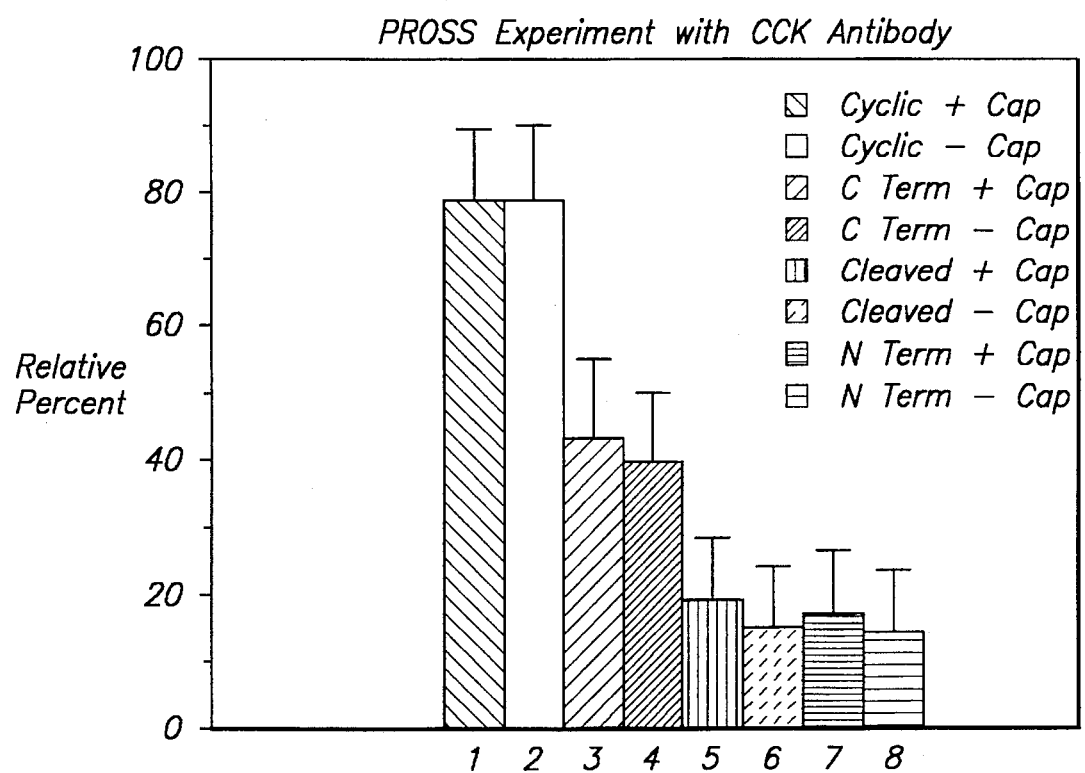
FIGS. 15a and 15b (SEQ ID NO: 11) are graphical representations of the cyclization and cleavage efficiencies, as measured by CCK antibody binding, for an array of cyclic and reversed polarity peptides.

A NVOC-aminocaproic slide was used for the following synthesis on the automated peptide synthesizer with the relative masking shown in the accompanying figure. A lithographic mask, as shown in FIGS. 14a and 14b, which illuminates approximately one half of the total area was employed in the first two steps. After photolysis and neutralization, the cyclization template NVOC—Glu—OFm was coupled to the surface. The initial mask was translated ¼ of distance to the side and an additional round of photolysis and neutralization was performed, followed by coupling of the cleavable linker on to the slide. This generated four sequences on the surface in roughly equal areas. The entire area was exposed to repetitive rounds of photolysis, neutralization, and amino acid coupling (BOP activation was employed) with the following amino acids: Phe, Asp, Met, Trp, Gly, and Met to produce the following general peptide sequences: Met-Gly-Trp-Met-Asp-Phe-Glu (SEQ ID NO: 10) and Met-Gly-Trp-Met-Asp-Phe (SEQ ID NO: 11) A lithographic mask which bisects the existing four regions was used to photolyze the slide. NVOC-aminocaproic acid was coupled to the surface after neutralization. The slide now contained eight different sequences on the surface. The entire area was photodeprotected and the side chain Fm protecting group removed with 40% piperidine in $CH_2Cl_2$. The entire slide was exposed to a 0.1 M solution of BOP (with HOBt and DIEA) for 2 hours at room temperature. After extensive washing, the slide was exposed to 90% TFA (with phenol, ethanedithiol, and thioanisole as scavengers) for 3 hours at room temperature to effect cleavage of the cleavable linker and remove the side chain protecting group of Asp. Non-specific protein binding to the slide was blocked with 1% BSA in PBS (BSA/PBS) for 1 hour, followed by washing. The slide was then exposed to the anti-cholescystokinin (CCK) antibody at a concentration of 5 μg/mL in BSA/PBS for 2 hours. After washing, the surface bound antibody was labeled by incubation with 10 μg/mL anti-mouse-FITC conjugate (Vector Labs) in BSA/PBS for 2 hours. The slide was washed 2×10 min in PBS and briefly in water and air dried. The surface was scanned for fluorescence as described elsewhere. The observed fluorescence counts are shown in bar graph form in the FIG. 15a.

The anti-CCK antibody is known to interact with the C-terminal region of the CCK peptide, and other experiments had established that 5 μg/mL of antibody was sufficient for high signal-to-noise scanning of immobilized peptide. The antibody exhibited higher binding to the regions on the slide where peptide reversal had taken place (indicated as "C term±cap"), and showed very little binding to the native (non-reversed, indicated as "N term±cap") peptide or to the regions where the peptide was completely cleaved from the surface (indicated as "Cleaved±cap"). Surprisingly, the antibody appears to recognize the intermediate cyclized (indicated as "Cyclic±cap") form of the peptide. The inclusion of a flexible linker (aminocaproic acid) appears to have little influence with this particular peptide-receptor combination.

Figure 15B:
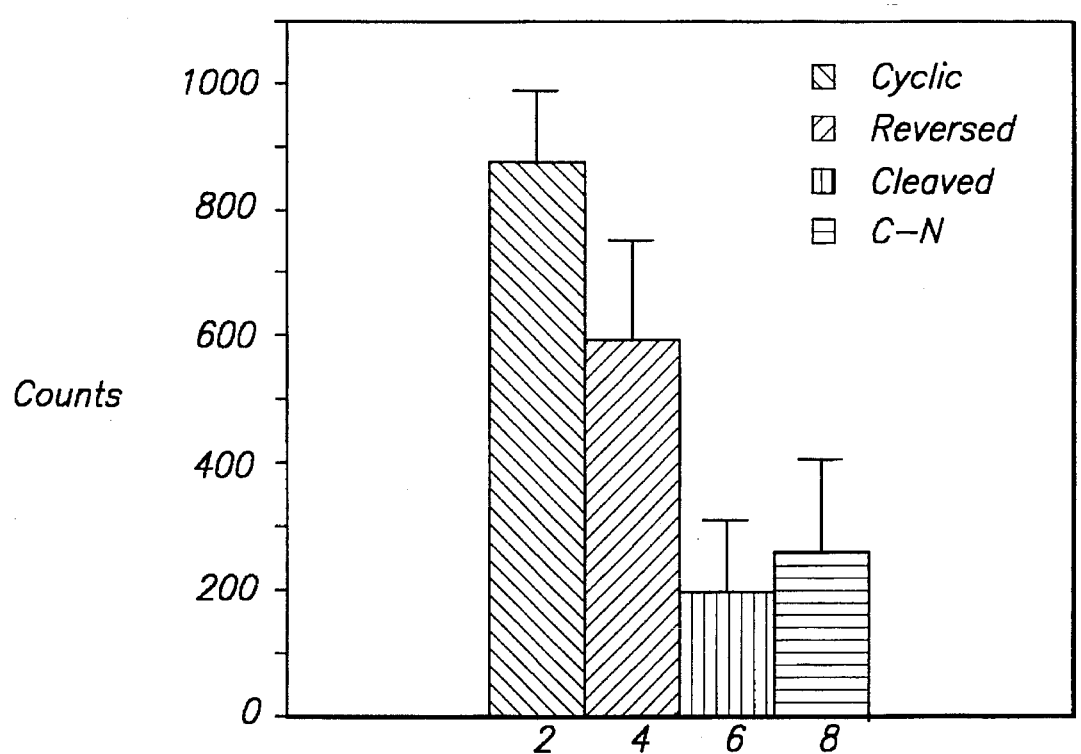

The experiment was repeated as described above with the exception that the cyclization step was performed with a different activator. The entire slide was exposed to a 0.1 M solution of HBTU (with HOBt and DIEA) for 5 hours at 55° C. The observed fluorescence counts are shown in bar graph form in FIG. 15b. Again, higher signal was observed for the reversed peptide than for the native peptide, indicative of reversal taking place as expected.

VI. Conclusion

It is seen that the above described methods and devices provide for improved and more versatile polymer synthesis on solid surfaces. It is to be understood that the above description is intended to be illustrative and not restrictive. Merely by way of example, the invention may be used in conjunction with the synthesis of a wide array of polymers, using a wide array of protective groups, and using a wide array of tether or link molecules. Also, there are numerous other applications that can readily be envisaged from the introduction of novel tethers into any solid-phase synthesis program. For example, one aspect of the invention would provide for a second orthogonal photocleavable bond as the anchor linking the first monomer to the support, allowing one to selectively cleave the assembled polymers off the surface. With the present invention, one can also simultaneously synthesize free N-terminus, cyclized, and free C-terminus peptides on a single solid support.

The scope of the invention should, therefore, be determined not with reference to the above description, but instead should be determined with reference to the appended claims along with their full scope of equivalents.

What is claimed is:

1. A method of synthesizing a polymer on a substrate comprising:

a) on a surface of said substrate attaching a molecule having the general formula $$\begin{array}{c} Y \\ | \\ T-X-PG \end{array}$$

where:

X is a first tether reactive site selected from the group consisting of O, NH, S, $CO_2$, S—$(CH_2)_nO$ and $NHCO(CH_2)_nCO_2$, where n is one to ten, Y is a second tether reactive site selected from the group consisting of:

1) O, NH, S, $CO_2$, S—$(CH_2)_nO$, and $NHCO(CH_2)_nCO_2$ functionality which functionality is blocked with a second protective group; and 2) OH, $NH_2$, SH, $CO_2H$, S—$(CH_2)_nOH$ and $NHCO(CH_2)_nCO_2H$ functionality, where n is one to ten, T is a tether molecule, and PG is a first protective group;

wherein the molecule is attached to the surface via a covalent bond between T and the surface;

b) removing any such second protective group employed on the second tether site Y while retaining the first protective group;

(c) coupling a polymer, said polymer having a first polymer reactive site and a second polymer reactive site, to said tether reactive site Y, wherein a bond is formed between said second polymer reactive site and said tether reactive site Y;

(d) removing said first protective group PG;

(e) coupling said first polymer reactive site to said tether at said first tether reactive site X; and (f) cleaving said bond between Y and the polymer whereby the polarity of the said polymer is reversed wherein said polymer is a linear, cyclic or branched chain polymer selected from the group consisting of peptides, nucleic acids and polysaccharides.

2. A method recited in claim 1 wherein said second tether reactive site, Y, is blocked with a second protective group and further wherein the procedure of coupling a polymer to said tether reactive site Y comprises:

i) removing said second protective group from said tether reactive site Y;

ii) coupling a first monomer to said tether reactive site Y, said first monomer having a monomer reactive site protected with a first monomer protective group;

iii) repeating said steps of removing a protective group and coupling a monomer to form a polymer at said tether reactive site Y, wherein said polymer has a first polymer reactive site and a second polymer reactive site and wherein said second polymer reactive site is coupled to said tether at said second tether reactive site.

3. A method of synthesizing a polymer on a substrate comprising:

a) on a surface of said substrate attaching a molecule having the general formula

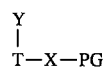

wherein:

X is a first tether reactive site selected from the group consisting of O, NH, S, $CO_2$, S—$(CH_2)_nO$, and $NHCO(CH_2)_nCO_2$, where n is one to ten, Y is a second tether reactive site selected from the group consisting of:

1) O, NH, S, $CO_2$, S—$(CH_2)_nO$, and $NHCO(CH_2)_nCO_2$ functionality which functionality is blocked with a second protective group; and 2) OH, $NH_2$, SH, $CO_2H$, S—$(CH_2)_nOH$ and $NHCO(CH_2)_nCO_2H$ functionality, where n is one to ten.

T is a tether molecule, and

PG is a first protective group;

wherein the molecule is attached to the surface via a covalent bond between T and the surface;

(b) removing any such second protective group employed on the second tether site Y while retaining the first protective group;

(c) coupling a polymer, said polymer having a first polymer reactive site and a second polymer reactive site, to said tether reactive site Y, wherein a bond is formed between said second polymer reactive site and said tether reactive site Y;

(d) removing said first protective group PC;

(e) coupling said first polymer reactive site to said tether at said first tether reactive site X; and (f) cleaving said bond between Y and the polymer whereby a polarity of the said polymer is reversed wherein said polymer is a linear, cyclic or branched chain peptide.

4. The method as recited in claim 2 wherein said first protective group is NVOC and said second protective group is selected from the group consisting of FMOC, allyl, and DMT.

5. The method as recited in claim 2 wherein said first protective group is selected from the group consisting of FMOC and DMT and said second protective group is NVOC.

6. The method as recited in claim 1 wherein said step of cleaving comprises the step of exposing said polymer to an acid.

7. The method as recited in claim 1 wherein said step of cleaving comprises the step of exposing said polymer to light.

8. A method as recited in claim 3 wherein said molecule having the formula

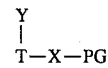

is an amino acid containing a protecting group PG on either the amino moiety or the carboxyl moiety.

9. A method as recited in claim 2 wherein said molecule having the formula

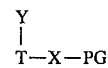

is a molecule having the general formula

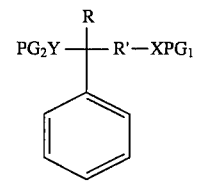

where:

X and Y are first and second reactive sites, respectively; $PG_1$ and $PG_2$ are first and second protecting groups, respectively; R is selected from the group consisting of hydrogen, methyl, phenyl, substituted phenyl, and bridged phenyl; and R' is selected from the group consisting of methyl, phenyl, substituted phenyl, and bridged phenyl.

10. A method as recited in claim 2 wherein said molecule having the general formula:

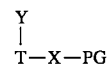

is a molecule having the general formula

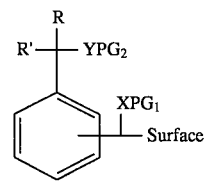

where:

X and Y are first and second reactive sites, respectively; $PG_1$ and $PG_2$ are first and second protecting groups, respectively; and R and R' are independently selected from the group consisting of hydrogen, methyl, phenyl, substituted phenyl, and bridged phenyl.

11. A method as recited in claim 2 wherein said molecule having the general formula:

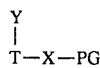

is a molecule having the general formula

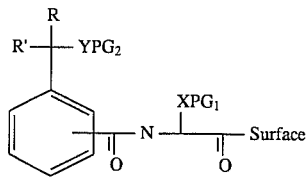

where:

X and Y are first and second reactive sites, respectively; PG$_1$ and PG$_2$ are first and second protecting groups, respectively; and R and R' are independently selected from the group consisting of hydrogen, methyl, phenyl, substituted phenyl, and bridged phenyl.

12. A method as recited in claim 2 wherein said molecule having the general formula:

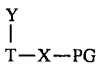

is a molecule having the general formula

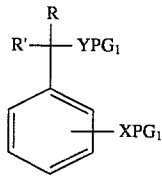

where:

X and Y are first and second reactive sites, respectively; PG$_1$ and PG$_2$ are first and second protecting groups, respectively; and R and R' are independently selected from the group consisting of hydrogen, methyl, phenyl, substituted phenyl, and bridged phenyl.

13. A method as recited in claim 2 wherein said molecule having the general formula:

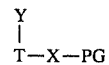

is a molecule having the general formula

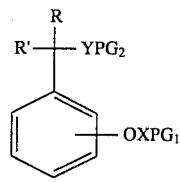

where:

X and Y are first and second reactive sites, respectively; PG$_1$ and PG$_2$ are first and second protecting groups, respectively; and R and R' are independently selected from the group consisting of hydrogen, methyl, phenyl, substituted phenyl, and bridged phenyl.

14. A method as recited in claim 2 wherein said first protective group PG is acid-labile and said second protective group is selected from the group consisting of base-labile and photoreactive protective groups.

15. A method as recited in claim 2 wherein said first protective group PG is base-labile and said second protective group is selected from the group consisting of acid-labile and photoreactive protective groups.

16. A method as recited in claim 2 wherein said first protective group PG is a photoreactive protective group and said second protective group is selected from the group consisting of acid-labile and base-labile protective groups.

* * * * *